Figure 1A:
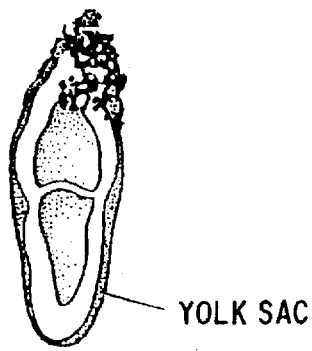

United States Patent [19]
Wagner et al.

[11] Patent Number: 5,744,347
[45] Date of Patent: Apr. 28, 1998

[54] YOLK SAC STEM CELLS AND THEIR USES

[75] Inventors: Thomas E. Wagner; Michael R. Antczak, both of Albany, Ohio

[73] Assignee: Ohio University Edison Biotechnology Institute, Athens, Ohio

[21] Appl. No.: 223,902

[22] Filed: Apr. 6, 1994

Related U.S. Application Data

[63] Continuation-in-part of Ser. No. 90,229, Jul. 9, 1993, abandoned, which is a continuation-in-part of Ser. No. 880,375, May 8, 1992, abandoned, which is a continuation-in-part of Ser. No. 730,250, Jul. 15, 1991, abandoned, which is a continuation-in-part of Ser. No. 4,077, Jan. 16, 1987, Pat. No. 5,032,407.

[51] Int. Cl.$^6$ ............................................. C12N 5/00
[52] U.S. Cl. ............................ 435/240.2; 435/240.21; 435/240.3; 435/7.21
[58] Field of Search ................ 435/240.2, 240.21, 435/240.3, 7.21

[56] References Cited

U.S. PATENT DOCUMENTS

| | | |
|---|---|---|
| 4,714,680 | 12/1987 | Civin . |
| 5,032,407 | 7/1991 | Wagner et al. . |
| 5,061,620 | 10/1991 | Tsukamoto et al. . |

OTHER PUBLICATIONS

McClanahan et al., 1993, "Hematopoietic growth factor receptor genes as markers of lineagecommitment during in vitro development of hematopoietic cells," Blood 81:2903–2915.
Huang and Terstappen, 1992, "Formation of haematopoietic microenvironment and haemopoietic stem cells from single human bone marrow cells," Nature 360:745–749.
Corn et al., 1991, "Culture and successful transplantation of embryonic yolk–sac cells," Clin. Biotech. 3:15–19.
Spangrude et al., 1991, "Mouse hematopoietic stem cells," Blood 78:1395–1402.
Tavassoli, 1991, "Embryonic and fetal hemopoiesis: An overview," Blood Cells 1:269–281.
Strojek et al., 1990, "A method for cultivating morphologically undifferentiated embryonic stem cells from porcine blastocysts," Theriogenol. 33:901–913.
Toles et al., 1989, "Hemopoietic stem cells in murine embryonic yolk sac and peripheral blood," Proc. Natl. Acad. Sci. USA 86:7456–7459.
Hollands, 1988, "Transplantation of embryonic haemopoietic stem cells without prior recipient X–irradiation," Brit. J. Haematol. 69:437–440.
Globerson et al., 1987, "In vitro differentiation of mouse embryonic yolk sac cells," Differentiation 36:185–193.
Kanamaru et al., 1987, "Characteristics of murine yolk sac erythroid progenitors and their population expansion in liquid culture," Int. J. Cell Cloning 5:134–141.
Flake et al., 1986, "Transplantation of fetal hematopoietic stem cells in utero: The creation of hematopoietic chimeras," Science 233:776–778.
Wong et al., 1986, "Properties of the earliest clonogenic hemopoietic precursors to appear in the developing murine yolk sac," Proc. Natl. Acad. Sci. USA 83:3851–3854.
Dick et al., 1985, "Introduction of a selectable gene into primitive stem cells capable of long–term reconstitution of the hemopoietic system of W/W$^v$ mice," Cell 42:71–79.
Kubai and Auerbach, 1983, "A new source of embryonic lymphocytes in the mouse," Nature 301:154–156.
Hsu, 1979, "In vitro development of individually cultured whole mouse embryos from blastocyst to early somite stage," Develop. Biol. 68:453–461.
Symann et al., 1978, "Murine yolk sac hematopoiesis studies with the diffusion chamber technique," Exp. Hemat. 6:749–759.
Weinberg and Stohlman, 1977, "Factors regulating yolk sac hematopoiesis in diffusion chambers: Various types of sera, cyclophosphamide, irradiation and long term culture," Exp. Hemat. 5:374–384.
Weinberg and Stohlman, 1976, "Growth of mouse yolk sac cells cultured in vivo," Brit. J. Haematol. 32:543–555.
Moore and Metcalf, 1970, "Ontogeny of the haemopoietic system: yolk sac origin of in vivo and in vitro colony forming cells in the developing mouse embryo," Brit. J. Haematol. 18:279–296.

*Primary Examiner*—Jasemine C. Chambers
*Attorney, Agent, or Firm*—Pennie & Edmonds LLP

[57] ABSTRACT

The present invention is directed to mammalian yolk sac stem cells. In particular, it relates to the characterization, culturing, long-term expansion and uses of yolk sac stem cells for in vivo reconstitution and therapy. Yolk sac stem cells isolated from the early embryonic yolk sac prior to blood island formation exhibit a homogeneous morphology and a primitive cell surface phenotype without the expression of mature leukocyte markers and major histocompatibility complex-encoded antigens. The cells can be cultured and expanded long-term with minimal differentiation, and without alteration of their pluripotency. However, such cells can be induced to express various blood cell markers upon stimulation with specific cytokines. In addition, the cells also express certain endothelial cell markers and growth characteristics. Such yolk sac cells may be particularly effective in the reconstitution of a lymphohematopoietic system, as they are capable of forming both endothelial cells and blood cells. Therefore, yolk sac stem cells may have a wide range of applications including but not limited to the reconstitution of a destroyed or deficient human hematopoietic system, and the construction of large and small animal models for the production of human blood cells, human antibodies, and testing of human diseases, immune function, vaccines, drugs and immunotherapy.

36 Claims, 26 Drawing Sheets

DAY 7

DAY 8.5

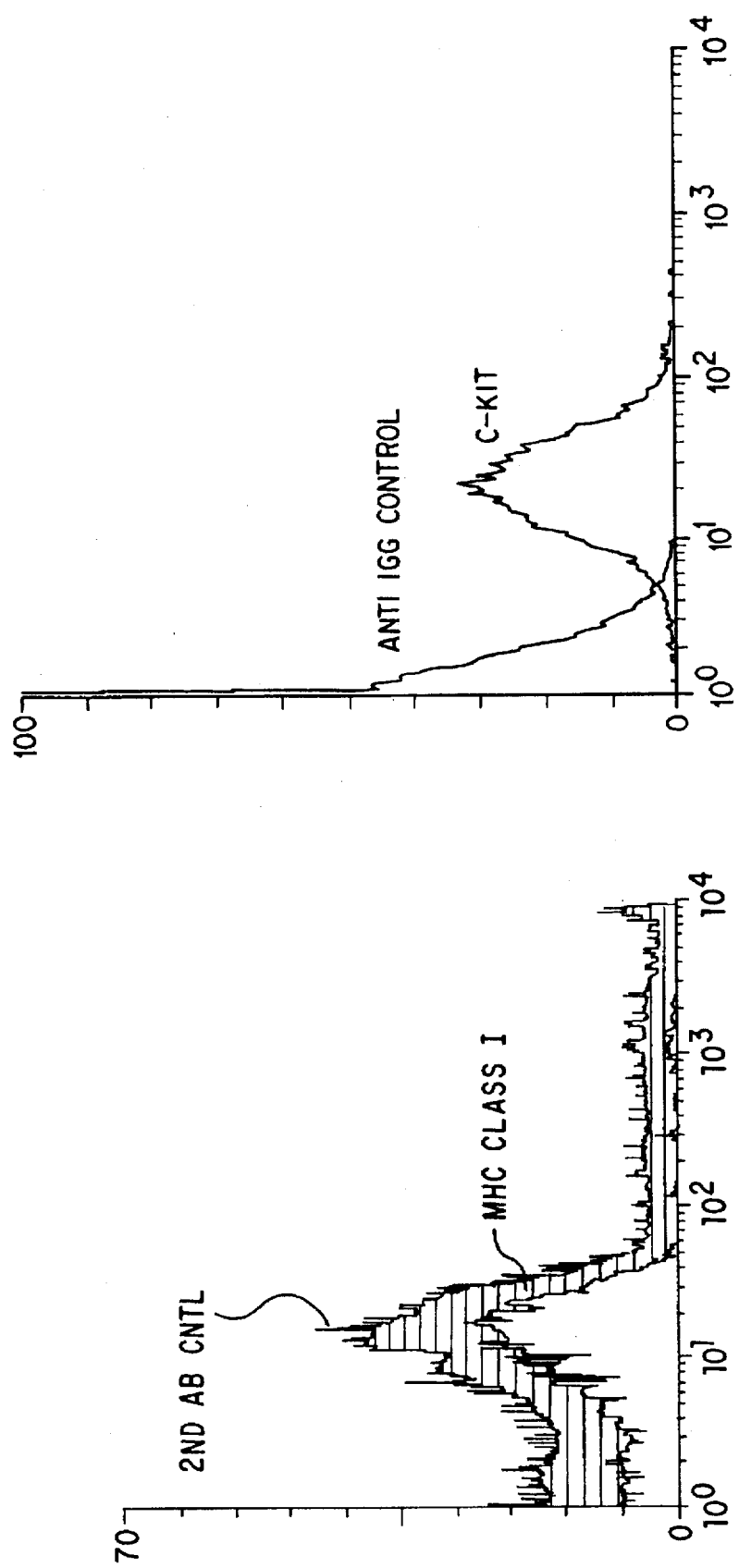

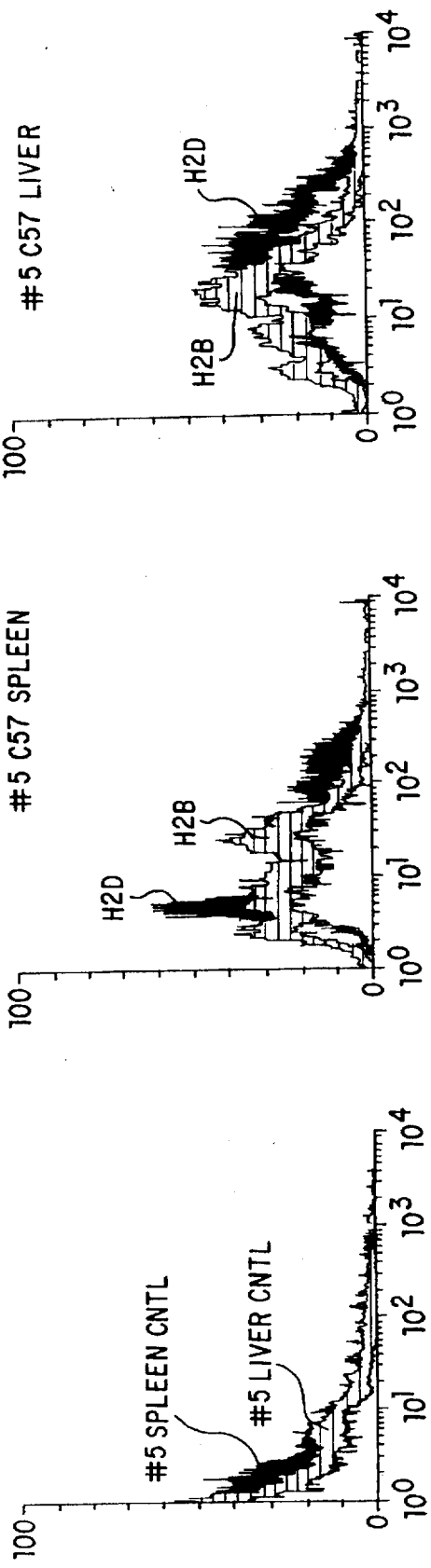

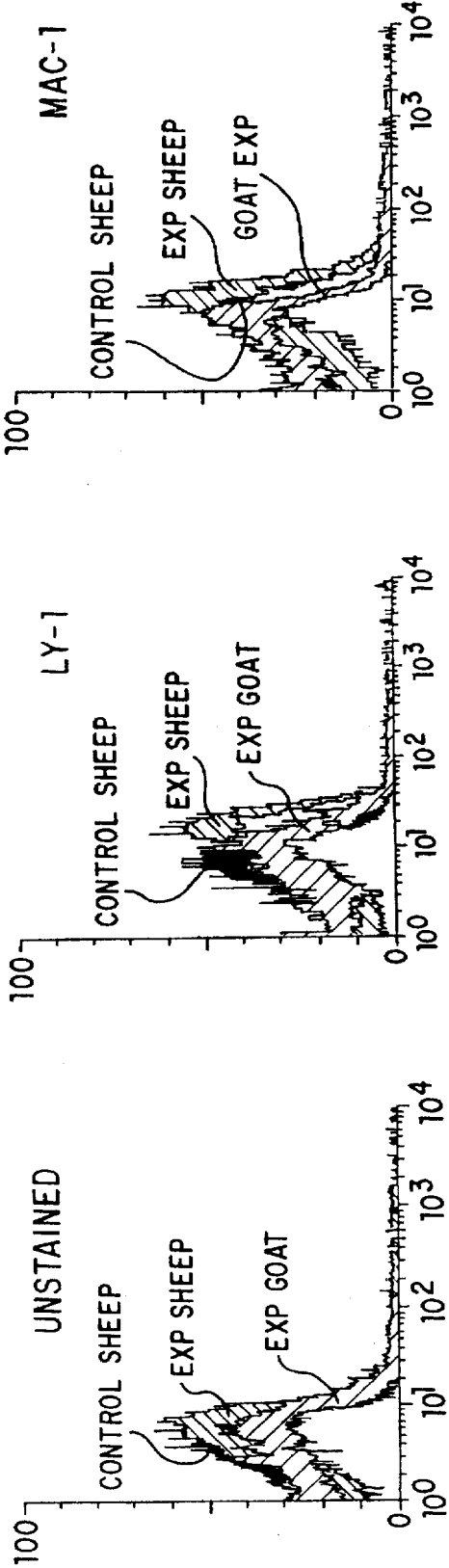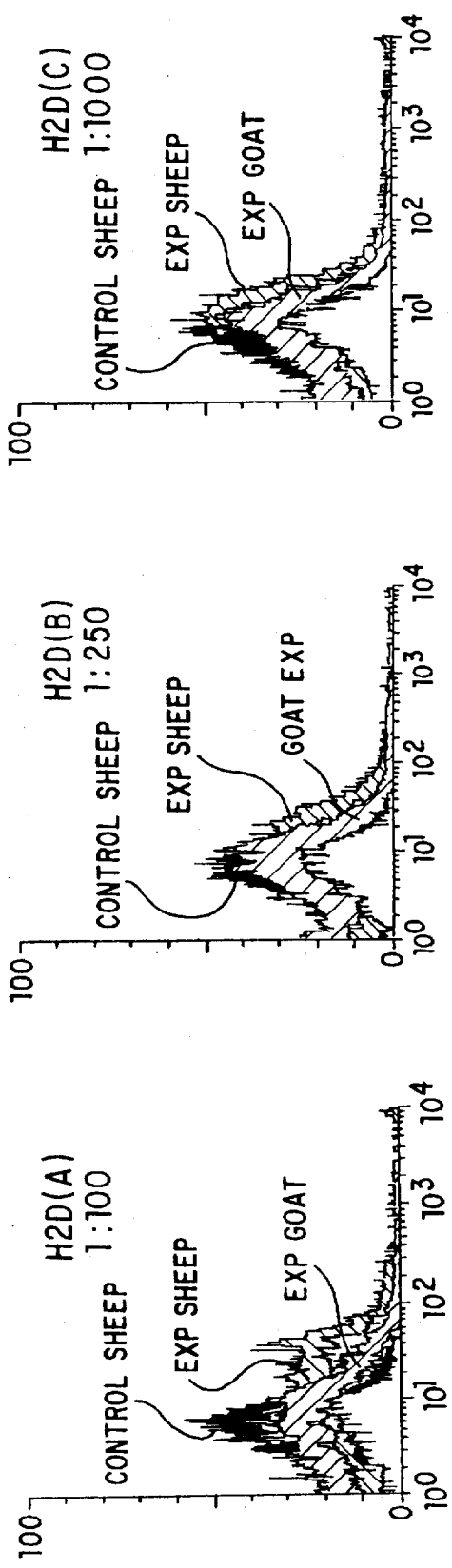
FIG. 17A FIG. 17B FIG. 17C FIG. 17D FIG. 17E FIG. 17F

YOLK SAC STEM CELLS AND THEIR USES The present application is a continuation-in-part of application Ser. No. 08/090,229 filed Jul. 9, 1993, now abandoned which is a continuation-in-part of application 07/880, 375, filed May 8, 1992 (Abandoned), which is a continuation-in-part of application Ser. No. 07/730,250, filed Jul. 15, 1991 (Abandoned), which is a continuation-in-part of application Ser. No. 07/004,077 filed Jan. 16, 1987, which issued as U.S. Pat. No. 5,032,407 on Jul. 16, 1991, each of which is incorporated by reference herein in its entirety.

TABLE OF CONTENTS

1. INTRODUCTION
2. BACKGROUND OF THE INVENTION
   2.1. HEMATOPOIETIC STEM CELLS 2.2. MAJOR HISTOCOMPATIBILITY COMPLEX
3. SUMMARY OF THE INVENTION
4. BRIEF DESCRIPTION OF THE DRAWINGS
5. DETAILED DESCRIPTION OF THE INVENTION
   5.1. ISOLATION OF YOLK SAC CELLS
   5.2. CHARACTERIZATION OF YOLK SAC CELLS
   5.3. FUNCTIONAL ACTIVITIES OF YOLK SAC CELLS
   5.4. USES OF YOLK SAC STEM CELLS
      5.4.1. HUMAN YOLK SAC CELLS IN MICE
      5.4.2. TRANSPLANTATION USING YOLK SAC CELLS
   5.5. BONE MARROW REPLACEMENT THERAPY IN HUMANS
   5.6. IDENTIFICATION OF NEW MARKERS ON YOLK SAC CELLS
6. EXAMPLE: GENERATION OF MURINE YOLK SAC STEM CELLS FOR IN VIVO HEMATOPOIETIC RECONSTITUTION
   6.1. MATERIALS AND METHODS
      6.1.1. ANIMALS
      6.1.2. ISOLATION OF THE EMBRYONIC YOLK SAC
      6.1.3. CULTURE CONDITIONS
      6.1.4. FLOW CYTOMETRY ANALYSIS
      6.1.5. INDUCTION OF YOLK SAC DIFFERENTIATION
      6.1.6. HEMAGGLUTINATION ASSAY
   6.2. RESULTS
      6.2.1. ISOLATION OF MURINE YOLK SAC CELLS
      6.2.2. CELL SURFACE PHENOTYPE OF YOLK SAC CELLS
      6.2.3. LONG-TERM MAINTENANCE OF YOLK SAC CELLS
      6.2.4. ENDOTHELIAL GROWTH CHARACTERISTICS OF YOLK SAC STEM CELLS
      6.2.5. DIFFERENTIATION OF YOLK SAC CELLS IN VITRO
      6.2.6. DIFFERENTIATION OF YOLK SAC CELLS IN VIVO
      6.2.7. GENERATION OF IMMUNOCOMPETENT CELLS BY YOLK SAC CELLS IN VIVO
      6.2.8. YOLK SAC CELLS REPOPULATE CHEMOABLATED MOUSE SPLEENS
      6.2.9. IN UTERO ADMINISTRATION OF YOLK SAC CELLS RESULTS IN TISSUE CHIMERISM
      6.2.10. XENOGENEIC TRANSPLANTATION OF YOLK SAC CELLS RESULTS IN LONG-TERM PERSISTENCE OF CELLS IN VIVO
7. EXAMPLE: GENERATION AND CHARACTERIZATION OF HUMAN YOLK SAC STEM CELLS
   7.1. MATERIALS AND METHODS
      7.1.1. ISOLATION OF THE EMBRYONIC YOLK SAC
      7.1.2. INDUCTION OF GLOBIN EXPRESSION
   7.2. RESULTS

1. INTRODUCTION

The present invention is directed to mammalian yolk sac stem cells. In particular, it relates to the characterization, culturing, long-term expansion and uses of yolk sac stem cells for in vivo reconstitution and therapy. Yolk sac stem cells isolated from the early embryonic yolk sac prior to blood island formation exhibit a homogeneous morphology and a primitive cell surface phenotype without the expression of mature leukocyte markers and major histocompatibility complex-encoded antigens. The cells can be cultured and expanded long-term with minimal differentiation, and without alteration of their phenotype and pluripotency. However, such cells can be induced to express various blood cell markers upon stimulation with specific cytokines. In addition, the cells also express certain endothelial cell markers and growth characteristics. Such yolk sac cells may be particularly effective in the reconstitution of a lymphohematopoietic system, as they are capable of forming both endothelial cells and blood cells. Therefore, yolk sac stem cells may have a wide range of applications including but not limited to the reconstitution of a destroyed or deficient human hematopoietic system, and the construction of large and small animal models for the production of human blood cells, human antibodies, and testing of human diseases, immune function, vaccines, drugs and immunotherapy.

2. BACKGROUND OF THE INVENTION

A multipotential stem cell population is capable of giving rise to blood cells of diverse morphology and function (Golde, 1991, Scientific American, December:86). Since blood cell formation is first detectable in the embryonic yolk sac early in embryogenesis, it has been hypothesized that pluripotent hematopoietic stem cells may be present within the yolk sac, but the characteristics of such cells are still poorly understood and such cells have not heretofore been identified (Moore and Metcalf, 1970, 18:279). During fetal development, the stem cells migrate to the fetal liver where they reside temporarily, and eventually move to give rise to the bone marrow which is the permanent site of blood cell formation in the adult. Studies on the development of blood cells have led to the identification of a variety of important growth and differentiation factors that regulate hematopoiesis. Further, tissue typing technology has ushered in dramatic advances in the use of hematopoietic stem cells as a form of therapy in patients with deficient or abnormal hematopoiesis.

2.1. HEMATOPOIETIC STEM CELLS

A pluripotent stem cell is believed to be capable of self-renewal and differentiation into blood cells of various lineages including lymphocytes, granulocytes, macrophages/monocytes, erythrocytes and megakaryocytes (Ikuta et al., 1992, Ann. Rev. Immunol. 10:759). The mechanism by which a stem cell commits to a specific cell lineage has not been fully elucidated. The mechanisms involved in stem cell replication without differentiation are also unknown. However, it is clear that such events must, in part, be influenced by a variety of growth and differentiation factors that specifically regulate hematopoiesis. Other factors which are not yet identified may also be involved (Metcalf, 1989, Nature 339:27). The commonly known hematopoietic factors include erythropoietin (EPO), granulocyte/macrophage colony-stimulating factor (G/M-CSF), granulocyte colony-stimulating factor (G-CSF), macrophage colony-stimulating (M-CSF), interleukin 1–12 (IL-1 to IL-12), and stem cell factor (SCF).

An understanding of hematopoiesis is critical to the therapy of hematopoietic disorders. Neoplastic transformation, immunodeficiency, genetic abnormalities, and even vital infections all can affect blood cells of different lineages and at different stages of development. For example, basic knowledge of blood cell development has contributed to the success of bone marrow transplantation in the treatment of certain forms of hematopoietic malignancies and anemias.

Conventional therapy utilizes whole bone marrow harvested from the iliac crest but this approach has certain limitations. Bone marrow stem cells are present at extremely low concentrations, and they may not be at the earliest stage of differentiation in order to give rise to all blood cell lineages. An impediment in bone marrow transplantation is the need for matching the major histocompatibility complex (MHC) between donors and recipients through HLA tissue typing techniques. Matching at major loci within the MHC class I and class II genes is critical to the prevention of rejection responses by the recipient against the engrafted cells, and more importantly, donor cells may also mediate an immunological reaction to the host tissues referred to as graft-versus-host disease. In order to facilitate graft acceptance by the host, immunosuppressive agents often have been employed, which render the patients susceptible to a wide range of opportunistic infections.

Hollands examined the in vivo potential of embryonic cells, and found that day 7 embryonic mouse cells could colonize the hematopoietic system of normal non-irradiated allogeneic mice (Hollands, 1988, British J. Haematol. 69:437). However, it was not clear which embryonic cell population actually contributed to this result, as total embryonic cells were used for in vivo transfer. In a study on the effects of in utero cell transfer, day 9 yolk sac cells were injected into syngeneic fetuses which differed from the donor cells only at the β-globin locus (Toles et al., 1989, Proc. Natl. Acad. Sci. U.S.A. 86:7456). The donor cells were shown to induce erythropoiesis. Both of these in vivo studies utilized freshly isolated cells from mouse embryos, and there was no suggestion that long-term cultured and expanded embryonic yolk sac cells could retain their pluripotency. Long-term culture methods for yolk sac cells involved the use of diffusion chambers embedded in vivo within the species of origin of the yolk sac tissue (Symann et al., Exp. Hemat. 6:749, 1978) or in vitro methods that led to malignant transformation of the yolk sac cells. For example, long-term yolk sac cell lines were established from day 10–13 mouse embryos, and they were shown to give rise to tumor cells at high frequency (Globerson et al., 1987, Differentiation 36:185). Therefore, the potential of tumor formation renders such long-term cultured cells undesirable for use in reconstitution therapy.

2.2. MAJOR HISTOCOMPATIBILITY COMPLEX

The MHC is a highly polymorphic complex of genes (Bach and Sachs, 1987, New Eng. J. Med. 317:489). It was first discovered by its close association with the phenomenon of transplantation rejection of tissue grafts. Subsequent studies conclusively demonstrated that antigens encoded by MHC class I genes are the major targets of transplantation rejection responses. Such antigens are expressed by all somatic cells.

MHC class II genes encode molecules on a limited array of cells, most of which are related to the hematopoietic system. They can also elicit reactions by allogeneic immune cells.

Studies on the expression of MHC antigens by embryonic yolk sac cells yielded inconsistent results. Billington and Jenkinson (Transplantation 18:286, 1974), working with cells of the yolk sac of 10–14 day mouse embryos, found that these cells expressed both H-2 and non-H2 (murine major and minor histocompatibility) antigens. The work of Patthey & Edidin (Transplantation 15:211, 1973), cited by Billington and Jenkinson, reported that H-2 antigens first appeared on day 7 embryos which could provoke a strong immune reaction, but the latter suggested that these antigens did not make an appearance in utero until day 9 or later. See THE EARLY DEVELOPMENT OF MAMMALS 219 (Balls and Wild, eds., Cambridge U.:1975). Heyner reported that H-2 antigens were detectable in day 7 mouse embryos (Heyner, 1973, Transplantation 16:675). Further, mouse yolk sac cells obtained at day 9 of gestation were shown to be capable of generating a graft-versus-host response in vitro (Hofman and Globerson, 1973, Eur. J. Immunol. 3:179). However, Parr et al. demonstrated that H-2 antigens were absent on the apical or the laterobasal membrane of the mouse yolk sac endoderm even at day 20 of pregnancy (Parr et al., 1980, J. Exp. Med. 152:945). Thus, no consensus has been established in regard to the antigenicity of yolk sac cells.

3. SUMMARY OF THE INVENTION

The present invention relates to yolk sac stem cells, methods of isolating and culturing yolk sac stem cells, and methods of using the long-term cultured yolk sac cells for reconstituting an allogeneic and xenogeneic hematopoietic system.

The invention is based, in part, on Applicants' discovery that both the murine and human yolk sac, isolated from embryos prior to extensive blood island formation contain a relatively homogeneous population of cells that express a primitive cell surface phenotype: CD34⁻, MHC class I⁻ and class II⁻. Such cells can be expanded in number by long-term in vitro culture with minimal differentiation, but can give rise to blood cells as measured by globin message expression, surface markers and morphology, when subsequently treated with the appropriate hematopoietic growth and differentiation factors. The same cells are also able to form tubular network structures characteristic of endothelial cells. Such structures release non-adherent cells that are morphologically similar to mature blood cells. Further, the long-term cultured murine cells also can mature into functionally competent blood cells in vivo, capable of mediating antigen-specific immune responses, repopulating lymphohematopoietic organs, and prolonging survival of animals with a destroyed hematopoietic system. The yolk sac cells of the invention can be successfully transplanted into allogeneic fetuses in utero and into non-immunosuppressed xenogeneic hosts, since these cells do not induce graft-versus-host and host-versus-graft reactions, and result in tissue chimerism. Long-term cultured yolk sac cells are also suitable recipients for the transfer and expression of exogenous genes.

The invention is described by way of examples in which both human and murine yolk sac cells are isolated, and their cell surface phenotype is characterized. The homogeneous population of yolk sac cells is expanded in long-term culture, and shown to retain its phenotype and pluripotency in vitro and in vivo. A wide variety of uses for the yolk sac cells are encompassed by the invention described herein.

4. BRIEF DESCRIPTION OF THE DRAWINGS

FIG. 1A. A schematic drawing of the appearance of a mouse embryo around day 7 of gestation.

Figure 1B:
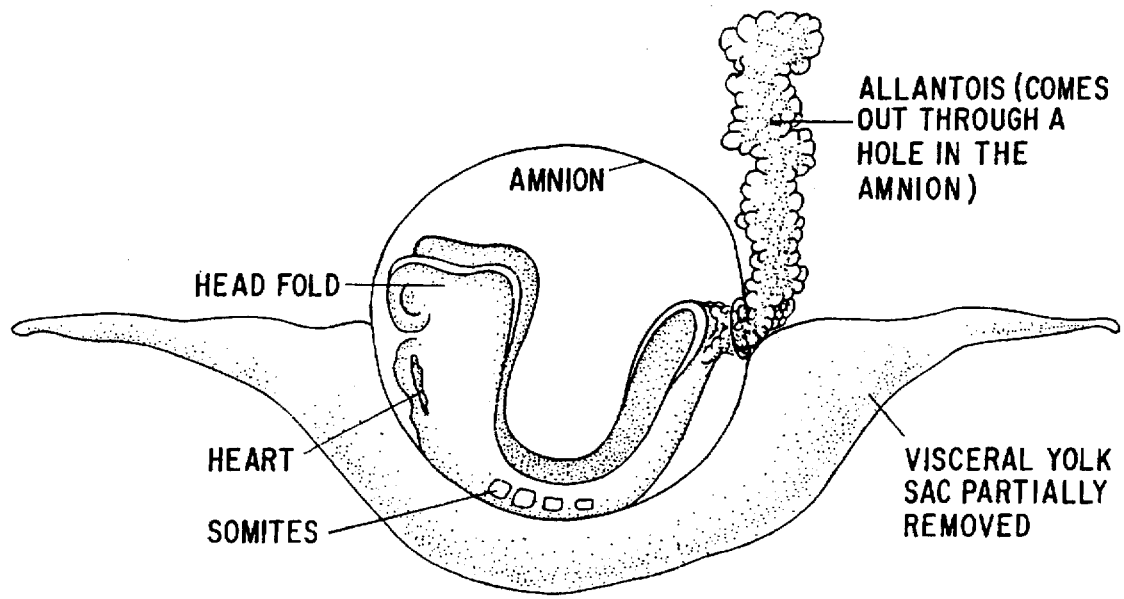

FIG. 1B. A schematic drawing of the appearance of a mouse embryo around day 8.5 of gestation.

Figure 2B:
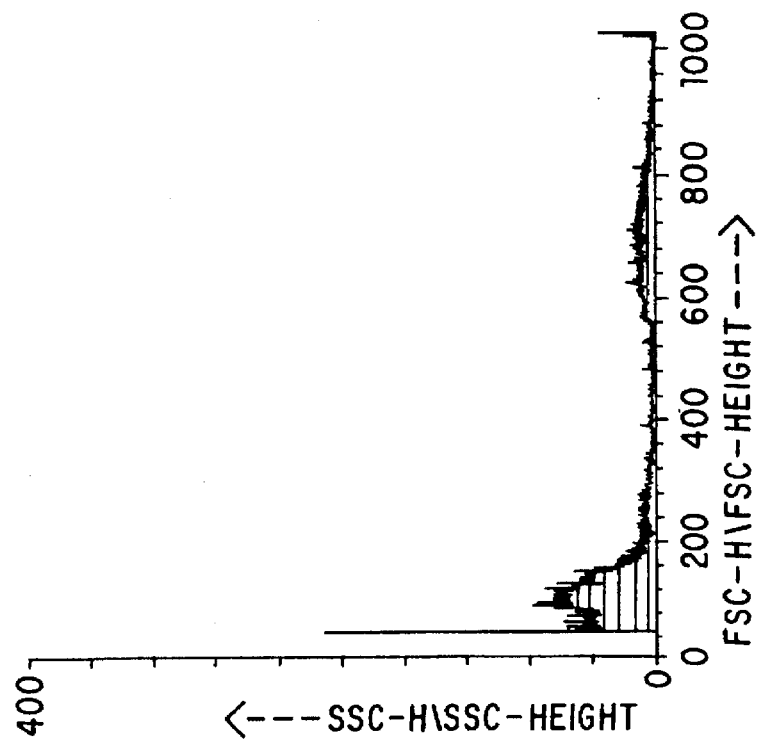
Figure 2A:
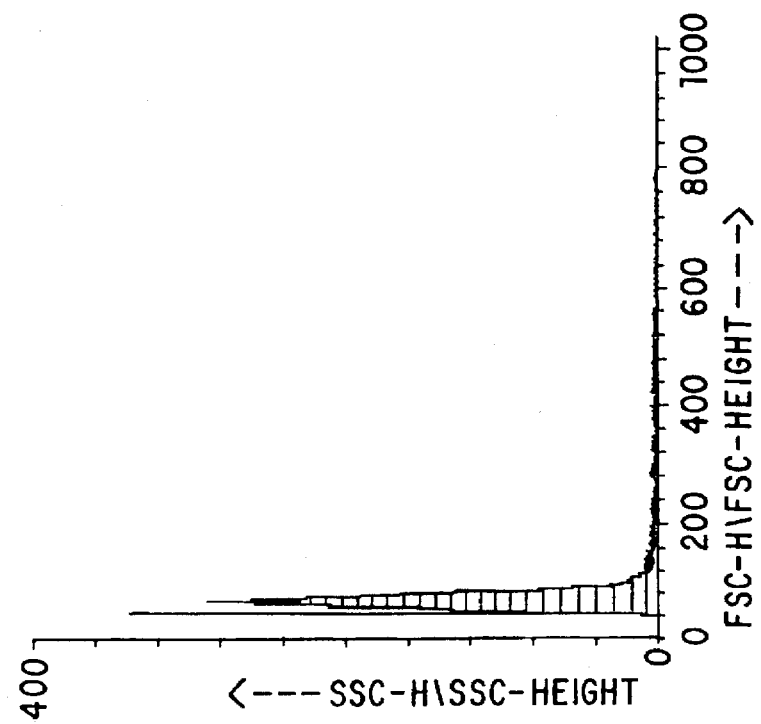

FIG. 2A. Murine yolk sac cells from a day 7 embryo are homogeneous in appearance.

FIG. 2B. Murine yolk sac cells from a day 8.5 embryo are heterogeneous.

Figure 3B:
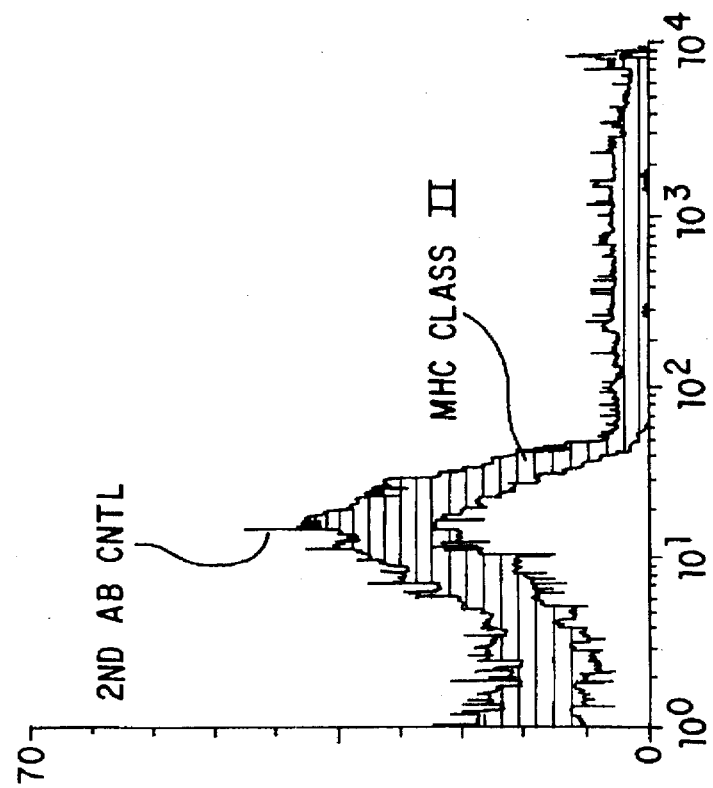
Figure 3A:
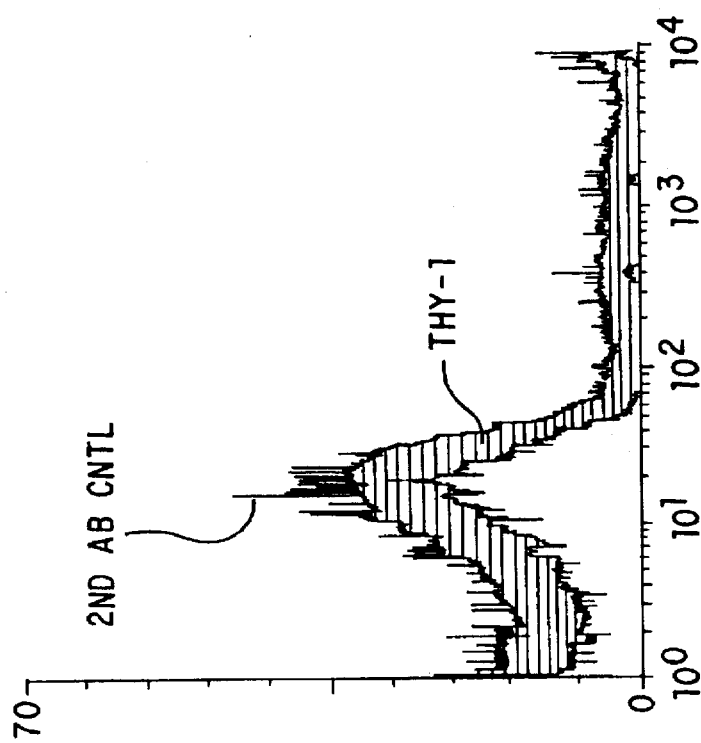

FIG. 3A. Murine yolk sac cells from a day 7 embryo do not express Thy-1 antigen by flow cytometry analysis.

FIG. 3B. Murine yolk sac cells from a day 7 embryo do not express MHC class II antigen.

FIG. 3C. Murine yolk sac cells from a day 7 embryo do not express MHC class I antigen.

FIG. 4. Murine yolk sac cells express c-kit by flow cytometry analysis.

Figure 5:
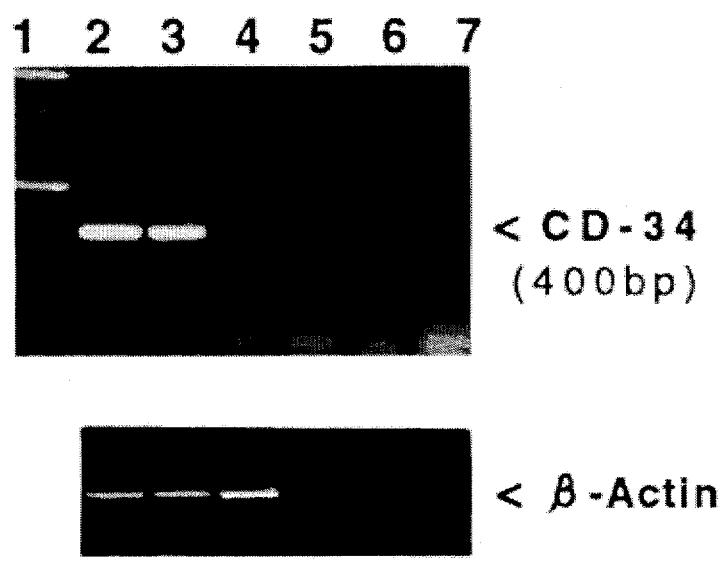

FIG. 5. Murine yolk sac cells do not express CD34 by reverse transcription-polymerase chain reaction (RT-PCR). Total RNA isolated from yolk sac cells (lanes 4 and 7), mouse myeloid leukemia cell line M1 (lines 2 and 5), and mouse bone marrow (lanes 3 and 6) was analyzed for CD34 expression using amplimers designed to amplify a 400 bp fragment of cDNA encoding a segment of the extracellular domain of the murine CD34 protein. RT-PCR reactions were performed in the presence (lanes 2, 3 and 4) and absence (lanes 5, 6 and 7) of reverse transcriptase to test for genomic DNA contamination. The amplification of $\beta$-actin by RT-PCR was used to demonstrate the integrity of each RNA preparation. DNA molecular weight markers consisting of a 100 bp ladder (Gibco-BRL) are shown in lane 1.

Figure 6A:
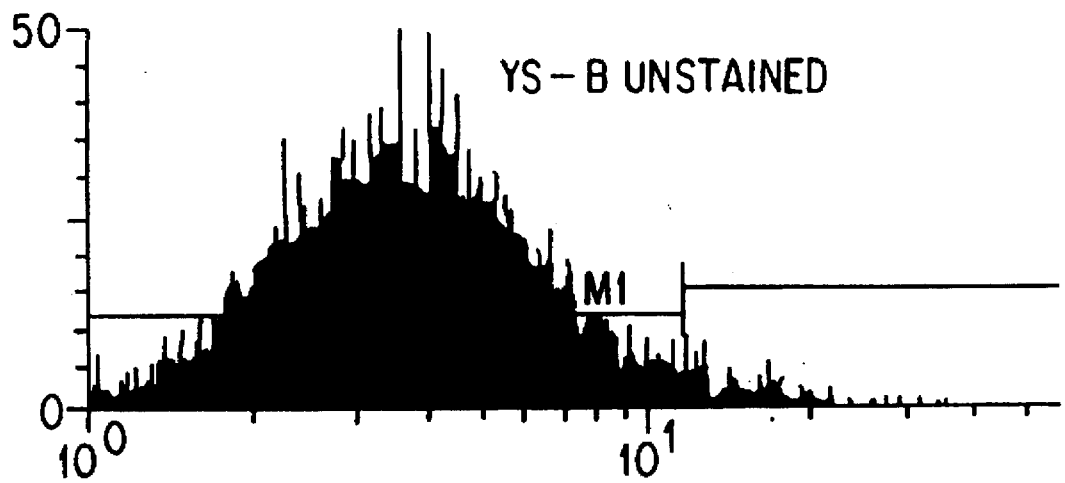

FIG. 6A. Unstained murine yolk sac cells as negative control.

Figure 6B:
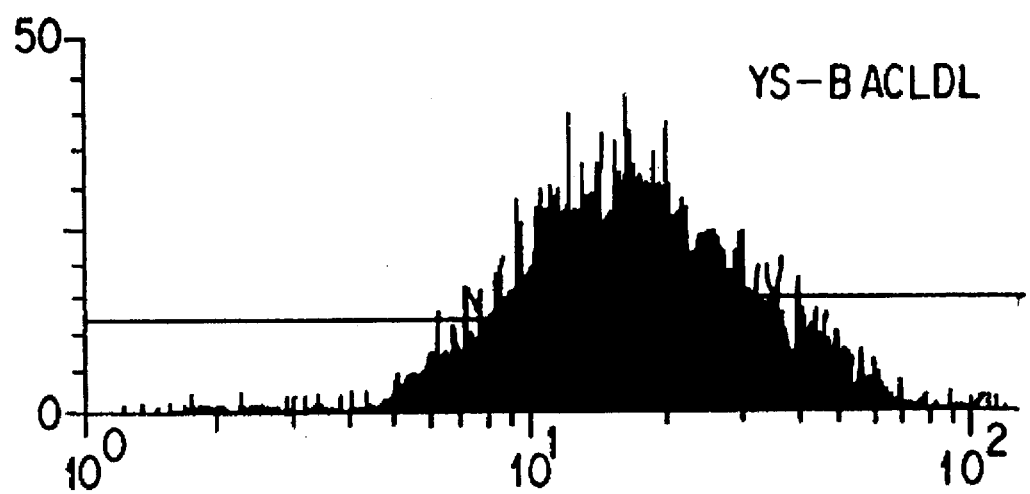

FIG. 6B Murine yolk sac cells internalize ac-LDL as measured by flow cytometry analysis.

Figure 7:
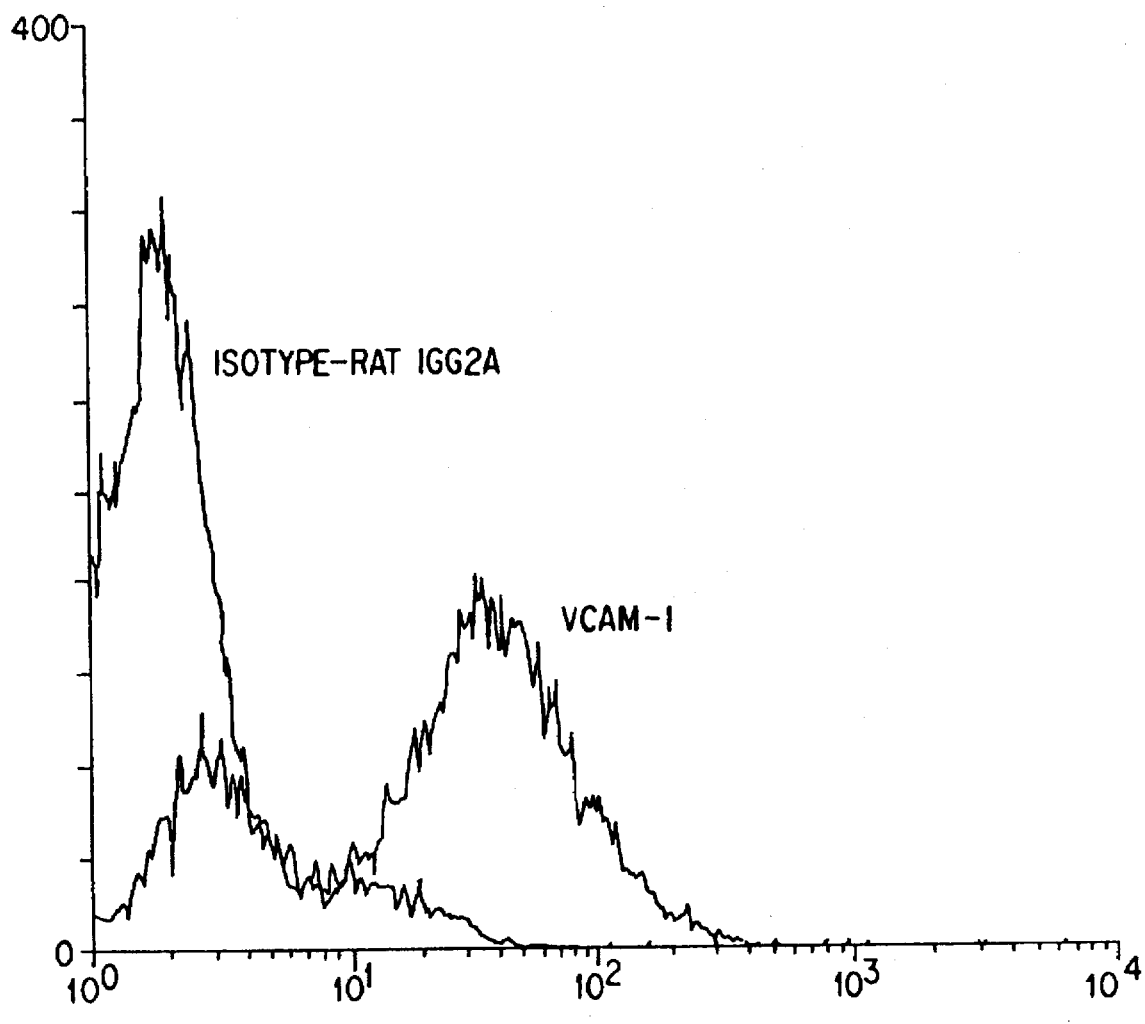

FIG. 7. Murine yolk sac cells express VCAM-1 by flow cytometry analysis.

Figure 8:
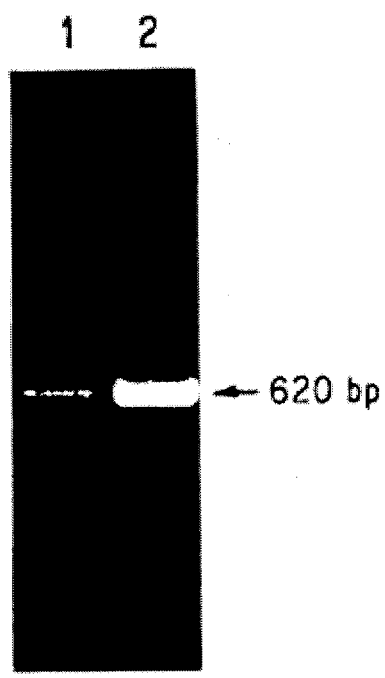

FIG. 8. Murine yolk sac cells express flk-1 by RT-PCR. Lane 1 is YS-EC, and lane 2 is E11.5 as positive control.

Figure 9:
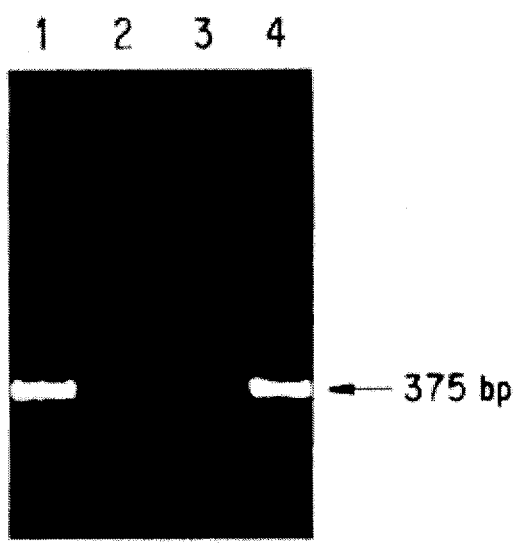

FIG. 9. Murine yolk sac cells express tek by RT-PCR. Lane 1 is YS-EC, lane 2 is Cos7, lane 3 is YS-EC (-RT), and lane 4 is Ell.5 as positive control.

Figure 10:
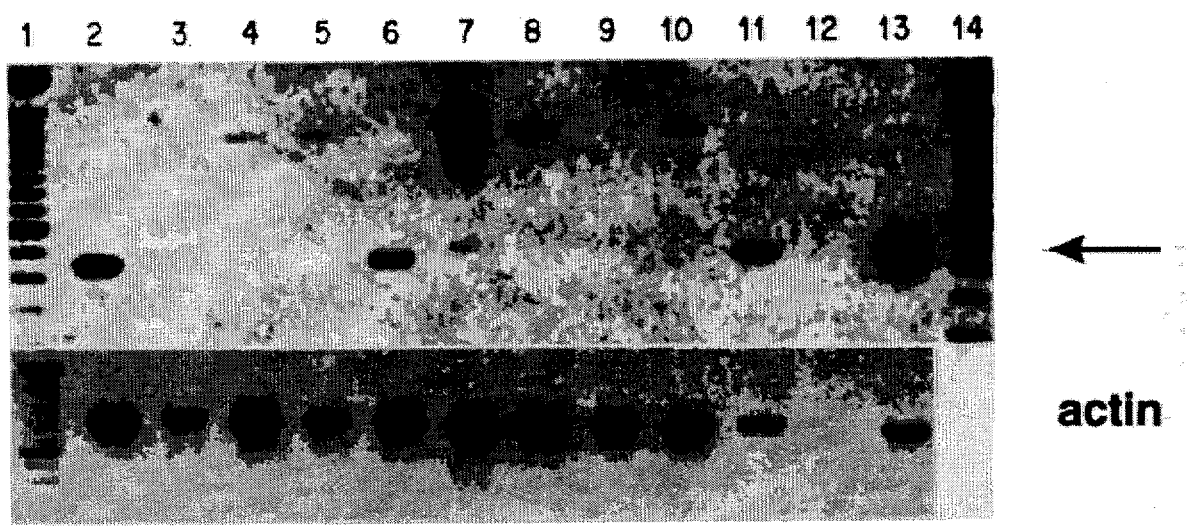

FIG. 10. Murine yolk sac cells express adult globin message when grown with SCF and EPO. Lane 2 is ES cell as positive control. Lane 13 is fetal liver as positive control. Both of these cell sources express adult $\beta$ globin message as indicated by the arrow. Lanes 4 and 5 are undifferentiated yolk sac cells. Lanes 6–11 are yolk sac cells induced to differentiate. The bottom half of the gel is actin control.

Figure 11:
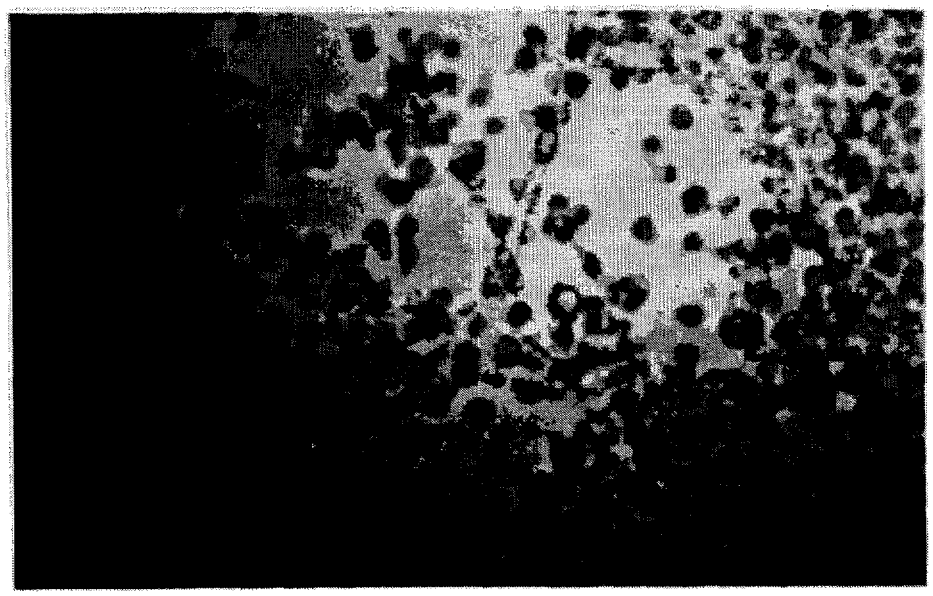
Figure 12A:
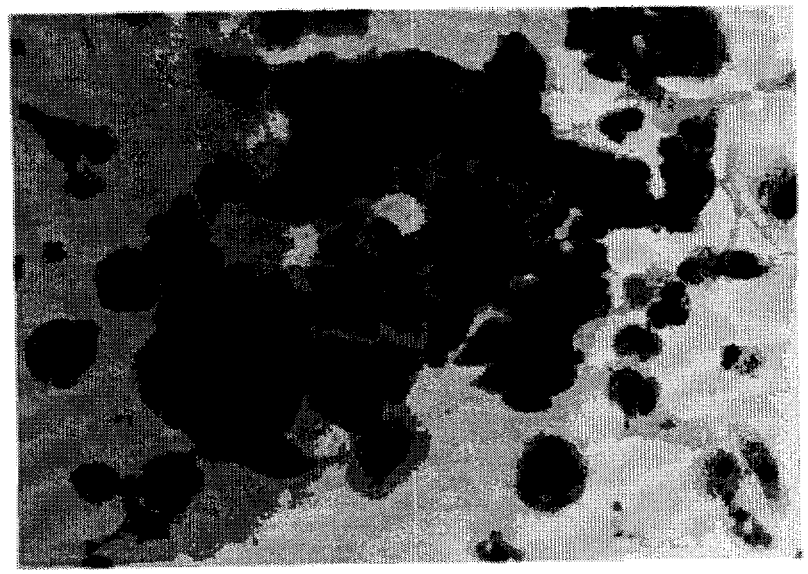
Figure 12B:
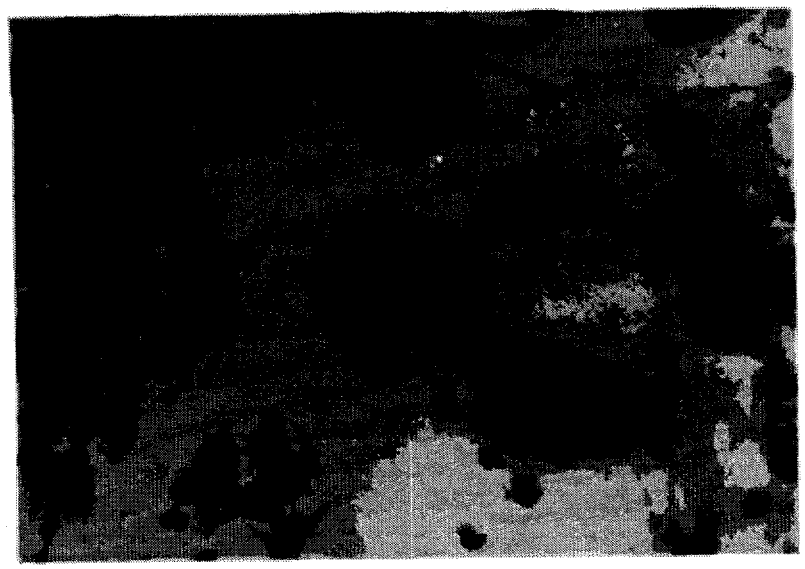
Figure 12C:
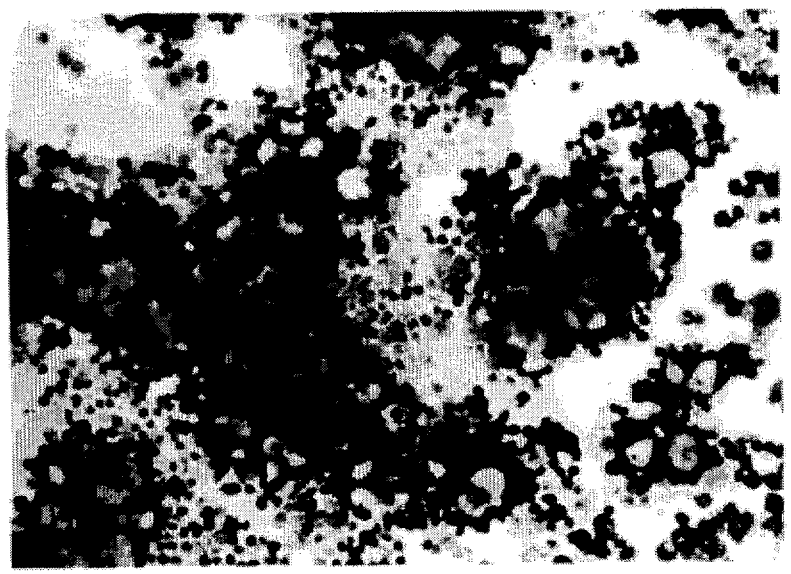
Figure 12D:
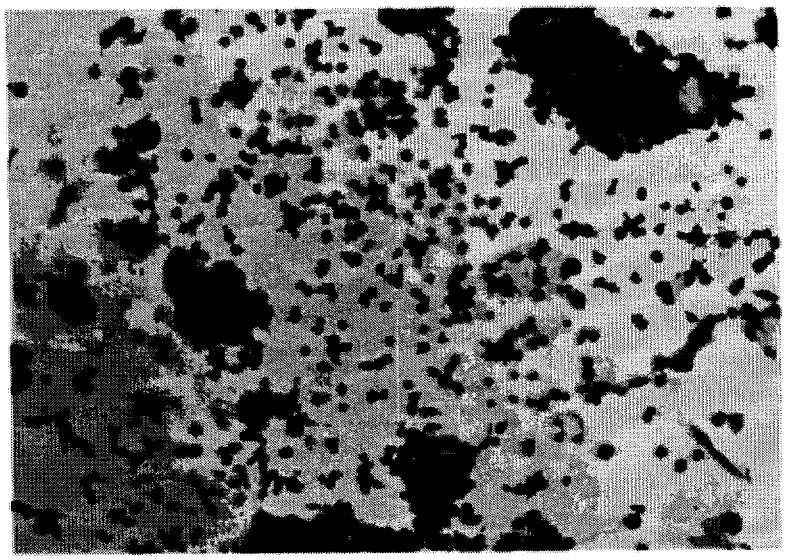

FIG. 11. Murine yolk sac cultures grown at high cell density give rise to tubular structures.

FIG. 12 A–D. Cultured murine yolk sac cells can differentiate into mature blood cells in vitro, including (12A) monocytes, and (12B) megakaryocytes, (12C) erythrocytes, (12D) lymphocytes.

Figure 13A:
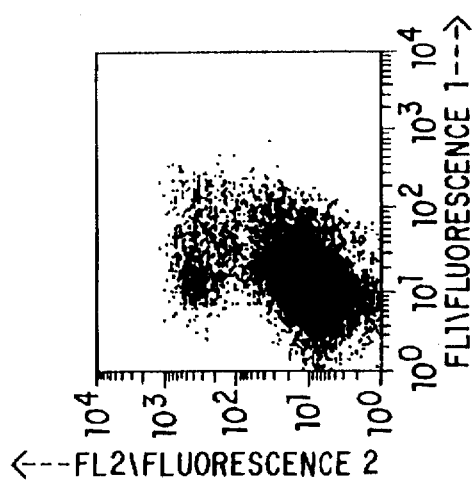
Figure 13B:
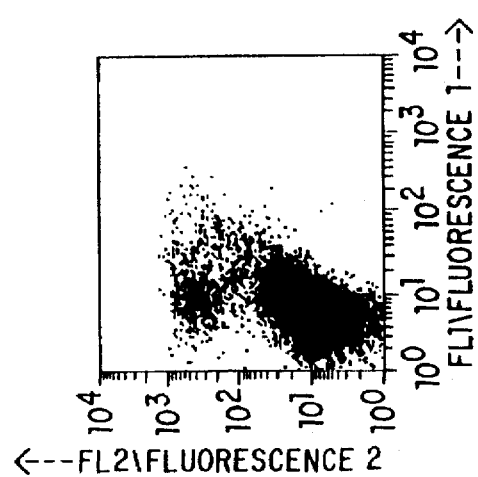
Figure 13C:
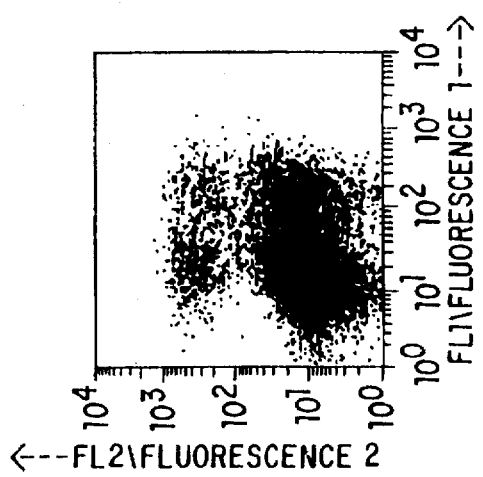
Figure 13D:
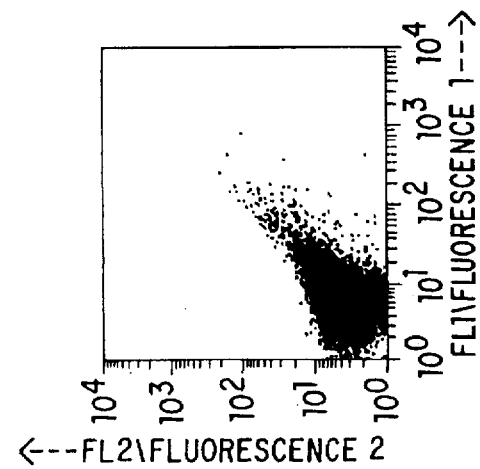
Figure 13G:
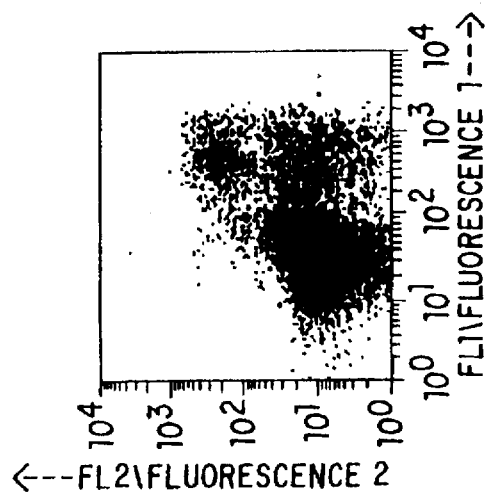
Figure 13F:
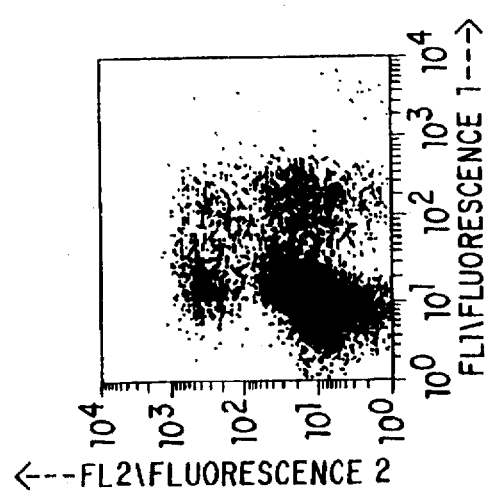
Figure 13E:
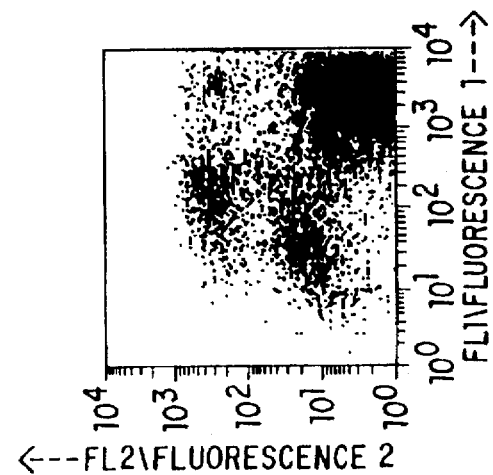

FIG. 13A–G. Yolk sac cells recovered from recipient mouse spleens following in vivo transfer demonstrate the expression of mature leukocyte antigens by donor cells. FIG. 13A is negative control. FIG. 13B are cells stained with anti-H-$2^d$. FIG. 13C are cells stained with anti-H-$2^d$ and IgG2a. FIG. 13D are cells stained with anti-H-$2^d$ and CD3. FIG. 13E are cells stained with anti-H-$2^d$ and Thy-1. FIG. 13F are cells stained with anti-H-$2^d$ and B220. FIG. 13G are cells stained with anti-H-$2^d$ and M1/70.

Figure 14A:
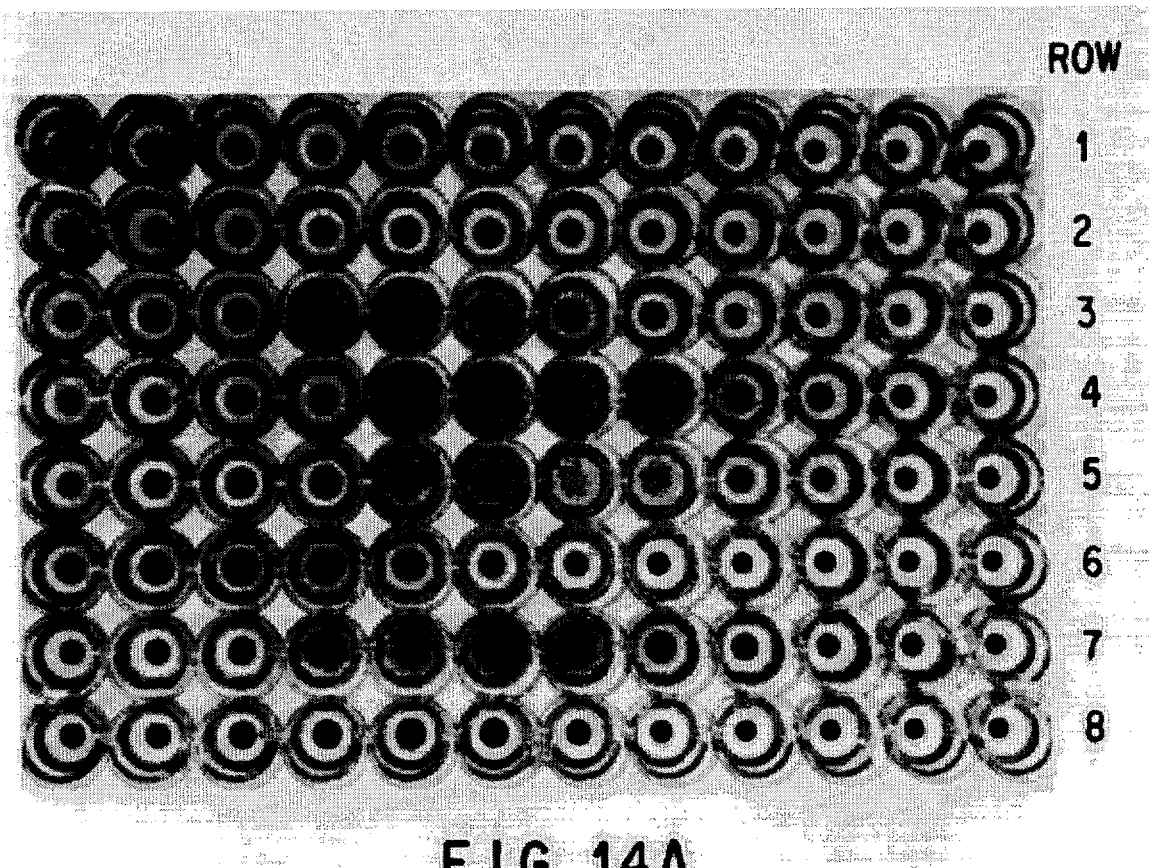
Figure 14B:
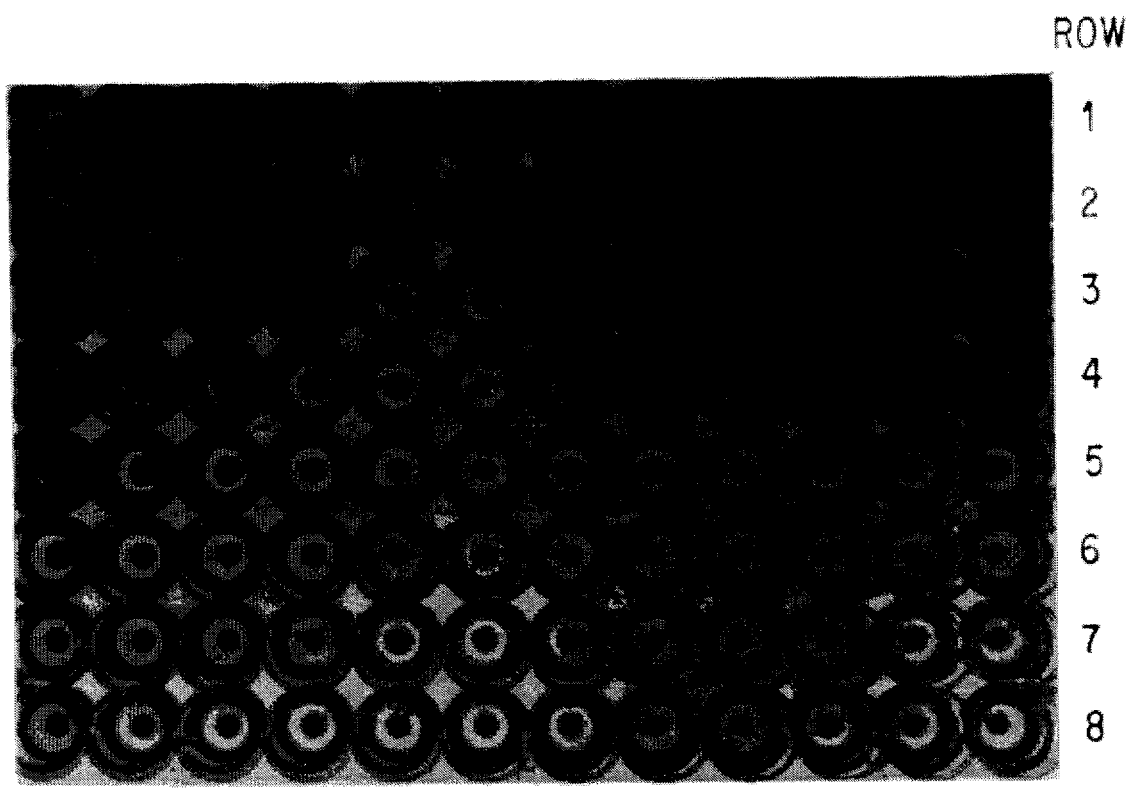

FIG. 14 A and B. Hemagglutination of red blood cells coated with antigens (FIG. 14A, lipopolysaccharide, and FIG. 14B, human serum albumin) by sera of immunodeficient mice treated with murine yolk sac cells, demonstrating restoration of immune function by yolk sac cells in vivo. In FIG. 14A, row 1 is serum from a normal mouse immunized with LPS, row 2 is serum from a BNX mouse without yolk sac cells, rows 3–7 are sera from BNX mice with yolk sac cells and immunized with LPS, and row 8 is negative control. In FIG. 14B, row 1 is positive control of serum from a C3H mouse immunized with HSA, row 2 is negative control of serum from a C3H SCID mouse, and rows 3–8 are sera from C3H SCID mice with yolk sac cells and immunized with HSA.

Figure 15A:
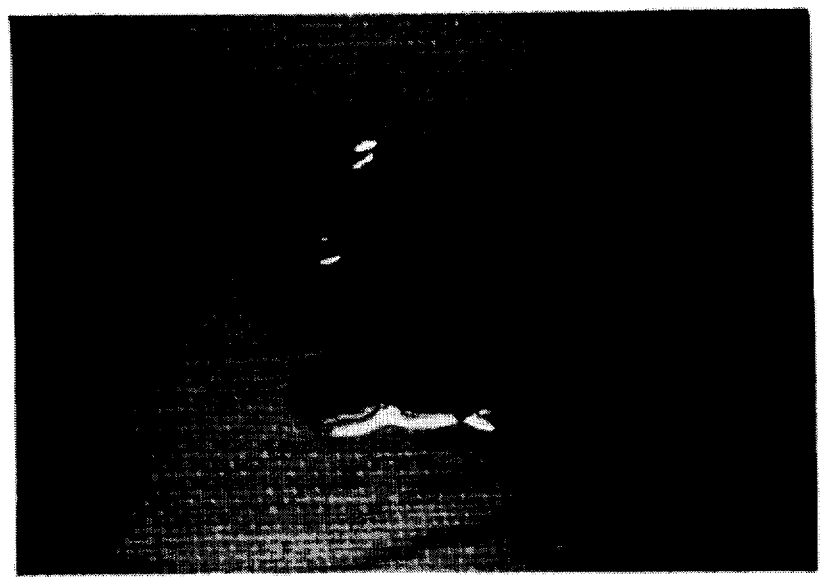
Figure 15B:
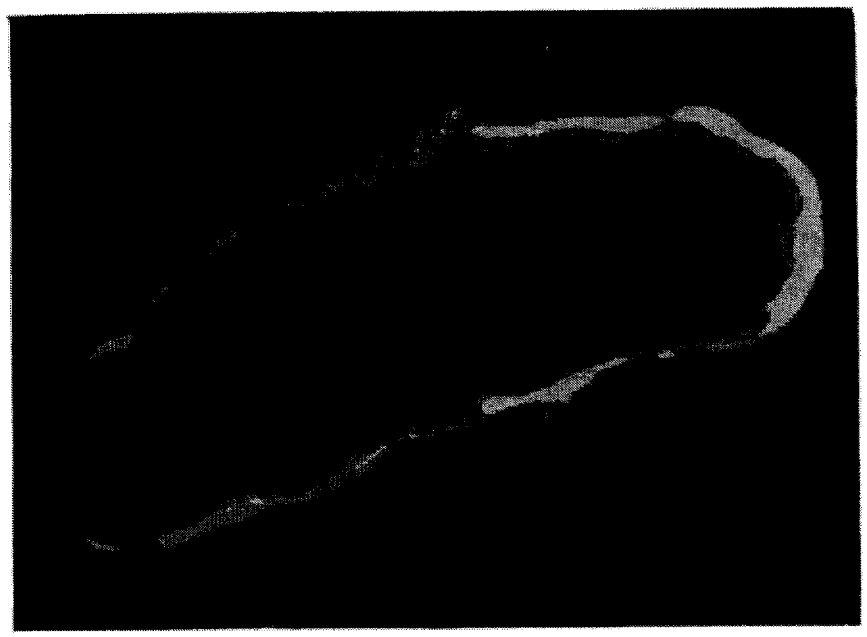
Figure 15C:
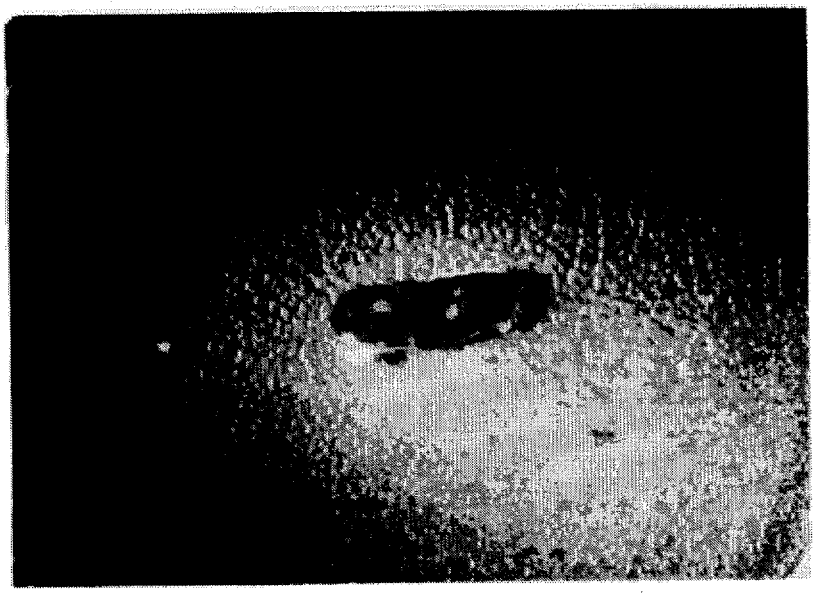

FIG. 15 A–C. Cultured murine yolk sac cells repopulate the spleens of chemically-ablated mice and give rise to colony-forming units in vivo; (15A) A comparison between a chemo-ablated mouse spleen and a fully repopulated spleen; (15B) A repopulated spleen at day 7 post-yolk sac treatment; (15C) A populated spleen at day 14 post yolk-sac treatment.

FIG. 16A–F. In utero injection of murine yolk sac cells into allogeneic mice leads to tissue chimerism in new born mice.

FIG. 17A–F. Survival and differentiation of long-term cultured murine yolk sac cells in a sheep and a goat which had received multiple high doses of yolk sac cells.

Figure 18:
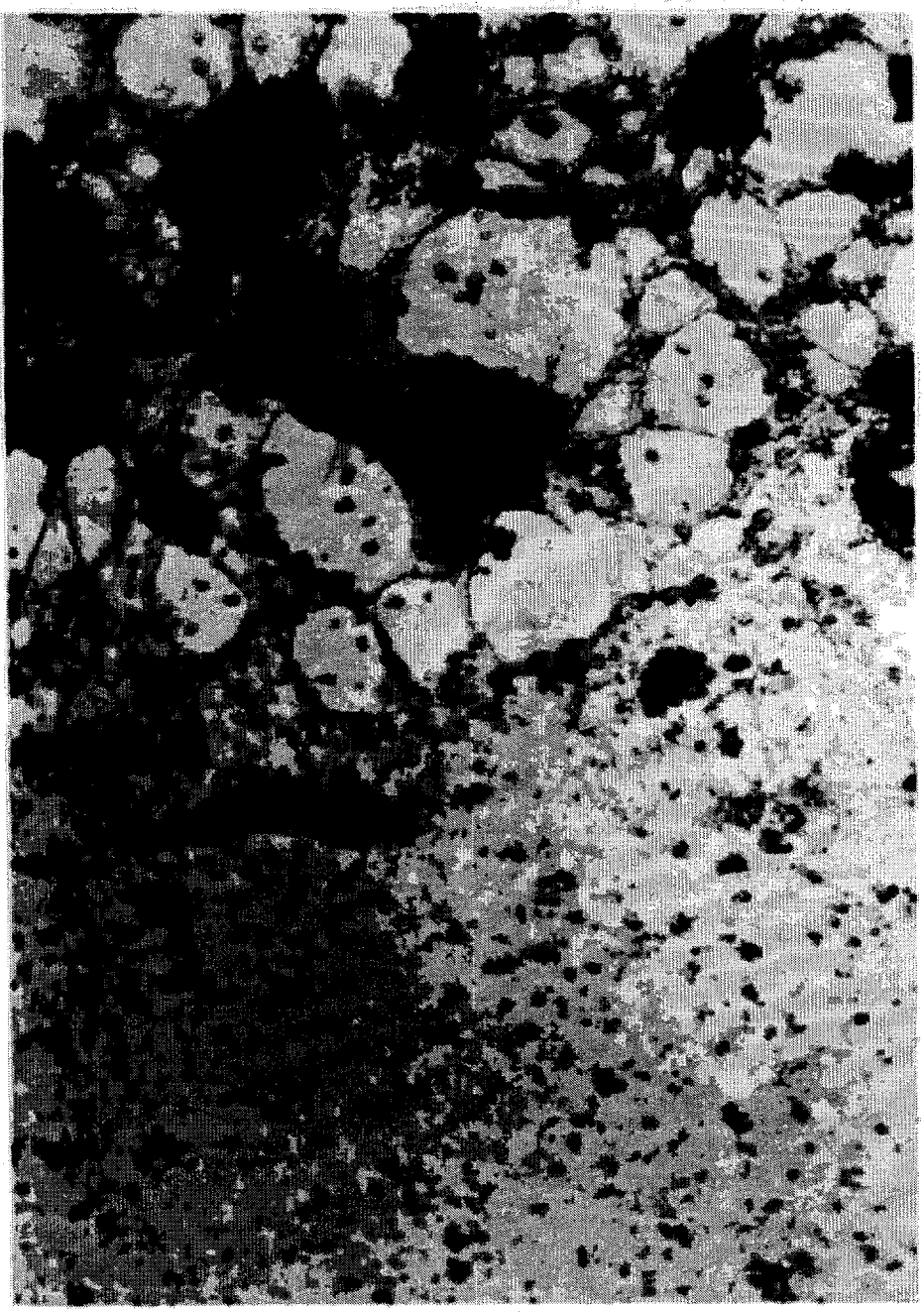

FIG. 18. Human yolk sac cells form tubular structures when cultured on "MATRIGEL"-coated surface.

Figure 19:

FIG. 19. Human yolk sac cultures give rise to non-adherent cells exhibiting mature blood cell appearance.

Figure 20A:
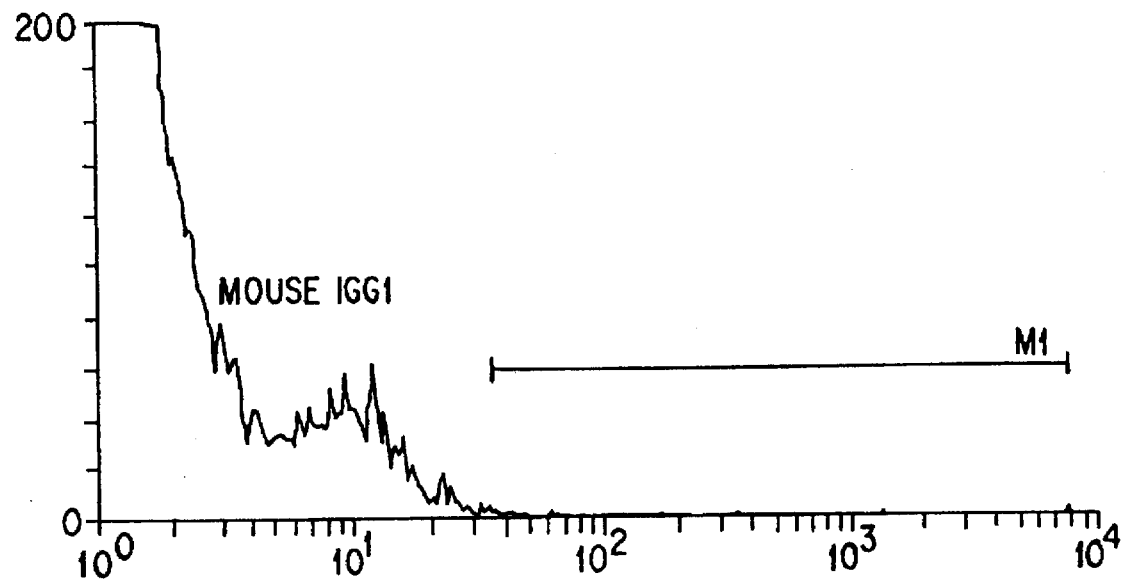

FIG. 20A. Human yolk sac cells stained with mouse IgG1 as negative control.

Figure 20B:
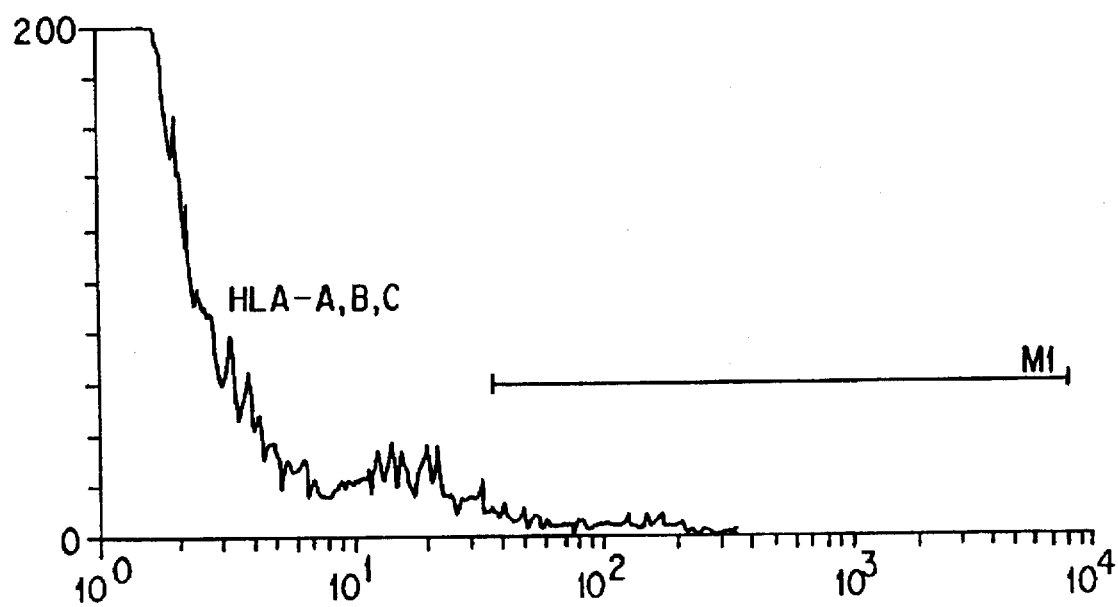

FIG. 20B. Most of the human yolk sac cells do not express HLA class I antigen by flow cytometry analysis.

Figure 21:
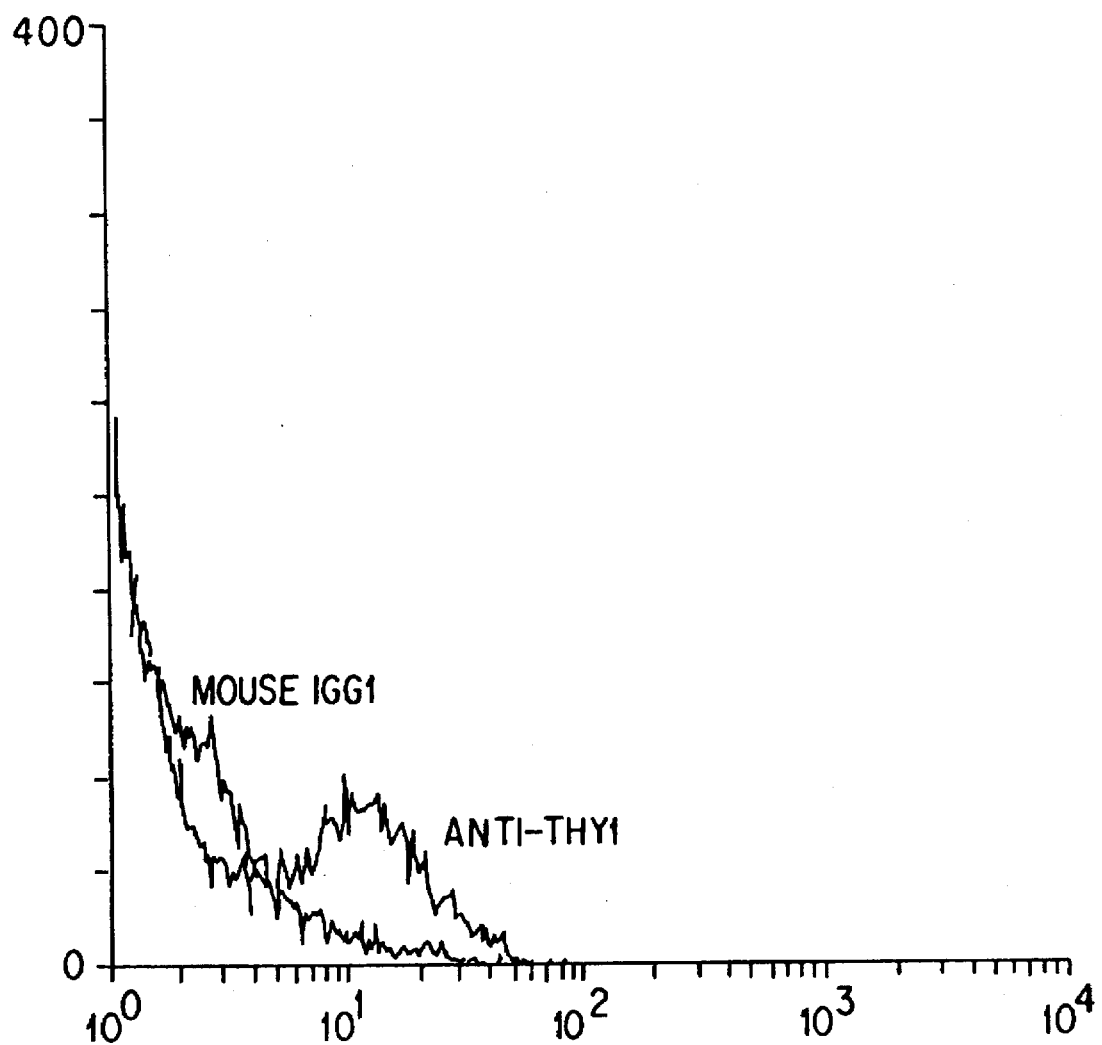

FIG. 21. Most of the human yolk sac cells are Thy-1$^-$, except for about 15% of Thy-1$^+$ cells.

Figure 22:
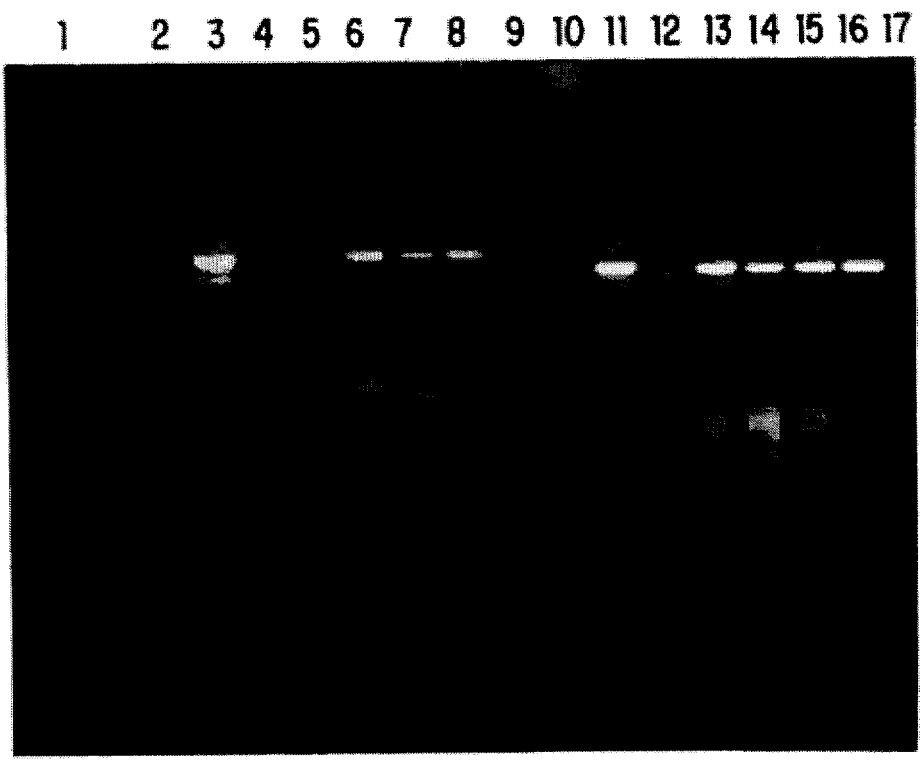

FIG. 22. Human yolk sac cultures express $\alpha$ and $\gamma$ globin message. Lane 1 contains molecular weight markers at 1000, 700, 500, 400, 300, 200, 100 and 50 base pairs. Lanes 2 and 10 are blank. Lanes 3 and 11 contain HEL 92.1.7 as Positive control. Lanes 4 and 12 contain KG1A as negative control. Lanes 5 and 13 contain cells grown in TGF$\alpha$(-LIF) medium. Lanes 6 and 14 contain cells grown in TGF$\alpha$ complete medium. Lanes 7 and 15 contain cells grown in IGF/FGF medium. Lanes 8 and 16 contain cells grown in total medium. Lanes 9 and 17 contain cells grown in base medium. Lanes 2–9 show herein $\alpha$ globin expression (PCR product at 451 bp). Lanes 10–17 show human $\gamma$ globin expression (PCR product at 390 bp). The bottom half of the gel shows negative controls from reactions without reverse transcriptase.

5. DETAILED DESCRIPTION OF THE INVENTION

The present invention relates to yolk sac stem cells, to methods of isolating and culturing the yolk sac stem cells, and to methods of using the yolk sac stem cells. The cells of the subject invention express both primitive hematopoietic and endothelial phenotype. In culture, they are able to give rise to endothelial tubular structures and mature blood cells.

Thus, the yolk sac stem cells described herein are a population of pluripotent hematopoietic/endothelial progenitor cells.

Although the specific procedures and methods described herein are exemplified using murine and human yolk sac cells, they are merely illustrative for the practice of the invention. Analogous procedures and techniques are equally applicable to all mammalian species, including but not limited to humans, baboons, monkeys, rabbits, hamsters, rats, etc. Therefore, mammalian yolk sac stem cells may be isolated from the embryonic yolk sac prior to blood island formation. The cells having the phenotype of $CD34^-$, and MHC class $I^-$ and $II^-$ may be cultured under the same conditions described herein, infra. Furthermore, while the cells of the invention originate in the yolk sac, such cells are known to be capable of migrating to other hematopoietic tissues. Thus, a cell population residing outside of the yolk sac, but expressing the same phenotype and functional characteristics as the yolk sac cells disclosed herein is also within the scope of the present invention. These include but are not limited to cells isolated from fetal liver, fetal bone marrow and adult bone marrow.

Mammalian development may be divided into three distinct stages: the zygote, from fertilization to cleavage; the embryo, from cleavage to the formation of all somites; and the fetus, from the formation of the last somite until birth. This invention takes advantage of the unique properties of embryonic yolk sac cells after their course of development is determined, but before they have lost either immunoincompetency or the ability to proliferate rapidly.

It is known that when completely undifferentiated cells of the blastula or morula are transplanted into a developed animal, they produce tumors. These totipotent, tumorigenic cells are of no value for in vivo reconstitution therapy. However, in accordance with the invention, it is advantageous to transplant cells which have reached a stage of specialization at which they have become committed to a particular sequence of development, or lineage. Such cells may be used alone or to deliver genetic material, or its expression products, into a particular tissue of the body, including blood cells and endothelial cells. The cells can be transplanted into a host before or after transformation with an exogenous gene of interest, and allowed to develop into the target tissue.

While it is necessary to use cells which have matured to the point of losing totipotency, fully mature cells will be rejected by a histoincompatible host. Consequently, it is desirable to use cells which have just lost totipotency, but still retain pluripotency for a particular tissue type. Such cells may also retain the ability to colonize, thus facilitating their delivery to the target tissue.

Stem cells of the embryonic yolk sac offer particular advantages for hematopoietic reconstitution. Unlike the cells of the embryo, the cells of the yolk sac develop into only a small number of different tissues. Among those tissues is the hematopoietic system, which includes the red and white blood cells, and the tissue of the veins, arteries and capillaries. Thus, by day 8 in the development of the mouse embryo, mesodermal cells in the yolk sac begin to form blood islands. The cells of the blood islands differentiate, the peripheral cells becoming the endothelium of the future blood vessels, and the central cells becoming first mesenchymal cells and then the red and white blood cells. The blood islands establish communications to form a circulatory network, which is extended into the embryo proper.

The yolk sac cells of the subject invention do not express MHC antigens, and can mature in allogeneic and xenogeneic hosts, demonstrating their ability to escape immune rejection. By contrast, research with bone marrow cells has depended on the use of immunocompromised hosts. The culture methods described herein maintain the yolk sac cells in their undifferentiated state, and are applicable to mass culture of yolk sac cells, providing donor cells for large numbers of recipients.

5.1. ISOLATION OF YOLK SAC CELLS

The embryonic yolk sac is the first identifiable site of blood cell formation in ontogeny. The yolk sac cells travel to the fetal liver during embryogenesis and eventually migrate to the bone marrow where they reside and differentiate into mature blood cells throughout the entire adult life.

The embryonic development of the mammalian yolk sac is rapid and occurs within a narrow time frame. For instance, the murine yolk sac is fully formed by day 7 of gestation. In primates, the formation of blood is detectable in the mesenchyme of the body stalk and in neighboring areas of the yolk sac. Shortly thereafter, masses of mesenchymal cells round up and become aggregated to form blood islands. By day 8.5, extensive blood island formation in the murine yolk sac is readily visible microscopically. At this stage, embryonic development has reached a level where fetal liver is beginning to develop and yolk sac cells begin to migrate to the fetal liver. Upon the departure of the yolk sac stem cells, the yolk sac begins to atrophy. Similar events also occur in embryonic development of other species, but the timing of developmental events varies between different species. In humans, the secondary yolk sac is formed between day 14 to 28 of gestation, and blood island formation also begins during this time period. Thus, human yolk sac cells isolated at this stage may be comparable to the murine cells at day 7. In addition, an earlier yolk sac known as the primary yolk sac is formed around day 10, which may also be used as a source of stem cells.

Since the yolk sac is where blood cell formation is first established in development and the yolk sac cells eventually reach the bone marrow to become the bone marrow hematopoietic cells, it is reasoned that the yolk sac represents the earliest site for the generation of primordial hematopoietic cell precursors. The cells have committed to a particular differentative pathway so that they are no longer totipotent. However, the yolk sac cells are still pluripotent, since they have not yet committed to a particular blood cell lineage as seen by their ability to make cells of lymphoid, myeloid, and erythroid lineages. In addition, the cells also possess endothelial potential. Hence, yolk sac cells may be the ideal cell population for use in reconstitution therapy including, but not limited to, bone marrow transplantation. In addition, the primitive nature of these cells, as evidenced by the absence of cell surface expression of various mature markers and MHC transplantation rejection antigens, may render these cells uniquely capable of being used as a universal donor cell population in allogeneic and even xenogeneic hosts. Furthermore, the ability of the cells of the invention to function as endothelial cells may provide additional advantages for their use.

The isolation of the embryonic yolk sac may be achieved using a variety of surgical methods. Traditionally, the yolk sac of a mouse embryo is disaggregated by the use of enzymatic digestion and mechanical separation upon surgical removal. A gentler method of detaching the cells from the yolk sac membrane and separating them from each other is described in Section 6.2.1. in which a yolk sac is immersed in an EDTA solution which causes the cells to segregate and form a single cell suspension. This method minimizes cell lysis due to physical force and cell surface protein alteration due to enzymatic treatment.

Since the establishment of blood islands in the yolk sac marks the beginning of cellular differentiation and blood cell formation, it is preferable that yolk sac cells be isolated prior to extensive blood island formation. Large numbers of highly homogeneous yolk sac cells of day 7 murine embryos (or similar stage human yolk sac cells), can be isolated using the method described herein, and cells obtained at this stage should in principle contain the least committed and least differentiated pluripotent stem cells suitable for long-term in vitro culture, for use in immediate in vivo therapy or as carriers of specific exogenous genes for use in gene therapy. In addition, yolk sac cells isolated in this manner may contain a relatively homogeneous population of stem cells that does not require further purification steps. Thus, most if not all of the cells may be capable of differentiating into mature blood cells and endothelial cells. This is in contradistinction to the bone marrow derived hematopoietic stem cells which are present in minute quantities in the bone marrow.

For long-term maintenance of the yolk sac cells, the cells are grown in medium containing a relatively high concentration of serum supplement, between 15–20%. The isolated yolk sac cells may be grown on a feeder layer of embryonic fibroblasts pretreated with mitomycin or irradiated to stop cell division. It is believed that embryonic fibroblast feeder layers produce, inter alia, leukemia inhibitory factor (LIF). In addition, various cytokines may be added in place of the feeder layers to suppress differentiation of the stem cells, including but not limited to, LIF, ciliary neurotrophic factor, oncostatin M (Conover et al., 1993, Development 119:559), epidermal growth factor, or stem cell factor/the c-kit ligand (SCF) or SCF in combination with other cytokines such as IL-3. Such factors may accelerate the multiplication of cultured cells, while inhibiting cellular differentiation in vitro. The examples presented, infra, were all performed using yolk sac cells grown in the presence of LIF. LIF may be used as conditioned culture media of LIF-producing cell lines which naturally secrete it or genetically engineered cell lines that express an exogenous LIF gene. Thus, LIF may be used in its natural or recombinant form, with or without further purification. The growth of cells using SCF could produce similar results. Alternatively, a number of other known hematopoietic factors such as IL-3, CSF's and EPO may also be used in combination depending on the need to select for a particular cell type. For example, the combined use of IL-3 and EPO may assist in driving cultured yolk sac cells towards the erythroid pathway. The maintenance of cells at the appropriate temperature, $CO_2$ concentration, humidity level and the frequency of changing the culture media are within the ordinary skill of the art.

In addition to surgical removal of a yolk sac for isolating yolk sac stem cells, such cell may be obtained by an in vitro blastocyst induction method as exemplified in 6.1.2.2. infra. During normal embryonic development, mammalian zygotes undergo cleavage and compaction to produce a morula. The morula is a round cluster of cells which consists of a small number of internal cells surrounded by a larger group of external cells. Most of the external cells become the trophoblast cells which do not contribute to forming embryonic structures. The descendants of the internal cells generate the inner cell mass (ICM) which eventually gives rise to the embryo proper. At the blastocyst stage, the trophoblast cells form the outermost layer, while the ICM is positioned in the interior, on one side of the ring of trophoblast cells.

The blastocyst induction method involves the early removal of embryos at the morula or blastocyst stage for in vitro culture. Such blastocysts can be developed in vitro to a precise stage when the yolk sac is formed so as to allow early isolation of yolk sac stem cells. The method described in Section 6.1.2.2., infra, utilizes "MATRIGEL" as substratum for the in vitro development of the blastocysts. On this surface and in the presence of specific cytokines, yolk sac cells are selectively encouraged to expand over other cells, and they eventually grow out of the blastocyst as the dominant cell population, without any surgical excision of the yolk sac. While a similar method was reported by Hsu (1979, Developmental Biology 68:453) who was able to culture murine blastocysts to early somite stage, Hsu's method does not describe how the growth of yolk sac cells can be selectively enhanced. In order to reduce trophoblast contamination, the blastocysts may be first treated with divalent ionophore for 10 to 30 minutes which causes selective lysis of trophoblast cells without damage to the ICM integrity. The ICM may be further processed by enzymatic treatment such as pronase. The blastocysts or isolated ICM can then be cultured on dishes coated with "MATRIGEL" and in medium containing various cytokines such as LIF, IL-3, IL-6 and EPO.

5.2. CHARACTERIZATION OF YOLK SAC CELLS

As shown by the examples described herein, yolk sac cells obtained from mouse embryos prior to blood island formation are more homogeneous in appearance than cells obtained from a later stage. Freshly isolated yolk sac cells from day 7 and day 8.5 murine embryos were compared by light scattering using flow cytometry analysis, see Section 6.2.1., infra. It is apparent that yolk sac cells of day 7 mouse embryos are extremely uniform with respect to both cell size and cell shape. By day 8.5, distinct populations of cells are clearly visible, suggesting that the earlier stage yolk sac cells may be clonally derived and the difference of 1 day in development may be critical to the nature of the yolk sac cells.

Another indication of the primitive nature of the early yolk sac cells is their cell surface phenotype in regard to the expression of various lineage-specific blood cell markers. This form of analysis may be most conveniently carried out by the use of a panel of marker-specific monoclonal antibodies. When the day 7 yolk sac cells were reacted with antibodies, the results showed that they lacked expression of all mature blood cell markers. In addition, such cells did not express MHC-encoded products which are the major targets of transplantation rejection responses. Thus, murine yolk sac stem cells can be characterized as c-kit$^+$, ac-LDL receptor$^+$, CD34$^-$, Thy-1$^-$, MHC class I$^-$ and MHC class II$^-$. Similarly, human yolk sac stem cells obtained from the primary yolk sac at about day 10 or the secondary yolk sac at day 14–28 may display a similar cell surface phenotype.

The CD34 and Thy-1 markers have been previously demonstrated to be associated with bone marrow hematopoietic stem cells (Spangrude et al., 1988, Science 241:58). While CD34 expression declines as stem cells differentiate and mature, the presence of Thy-1 is retained and its density increased in certain mature blood cells, particularly T-lymphocytes. The finding that yolk sac stem cells are negative for CD34 expression indicates that the yolk sac cells may represent an earlier cell population than the bone marrow stem cells which express CD34 and low levels of Thy-1 in the bone marrow microenvironment.

MHC-encoded class I and class II molecules are involved in immune regulation between T, B, and antigen presenting cells. The high level of polymorphism of these molecules also serve as targets in major transplantation rejection responses between genetically mismatched individuals. Therefore, HLA tissue typing is currently a routine clinical procedure in ensuring graft acceptance in human transplant patients by matching the donors and recipients at the major MHC genetic loci. The absence of MHC antigens on the yolk sac cell surface strongly suggests the possibility of using such cells as universal donors in hematopoietic reconstitution therapy, alleviating the need of tissue typing and the restrictive use of only MHC-matched tissues as donor cells. The development of adoptively transferred yolk sac cells in the environment of the host may lead to specific tolerance between the host and donor cells for each other, causing a diminution of the potential for inducing graft-versus-host and host-versus-graft reactions.

The above-described yolk sac phenotype is seen with the vast majority of cells isolated from day 7 murine embryos. Therefore, early isolation of yolk sac cells provides for a relatively homogeneous and enriched population of stem cells. This is in contradistinction to the extensive purification procedure needed for murine bone marrow hematopoietic stem cells which are of $CD34^+$ and $Thy-1^+$ phenotype. Such cells must be isolated and enriched by a series of selection steps, as they only constitute less than 0.1% of the total cells in the bone marrow (Spangrude et al., 1991, Blood 78:1395). On the other hand, yolk sac stem cells can be obtained in an essentially homogeneous state without requiring additional purification, and such cells retain their phenotype and functional activity during long-term in vitro growth. If cells displaying the same phenotype and characteristics as the yolk sac cells exist in other tissues, they are likely to be present in very low numbers, in which case they may require isolation by affinity purification based on their phenotypic profile.

5.3. FUNCTIONAL ACTIVITIES OF YOLK SAC CELLS

The pluripotency of yolk sac stem cells to differentiate and mature into functionally competent blood cells of various hematopoietic lineages was tested by a number of in vitro and in vivo methods described herein. The presence of a pluripotent population in long-term cultured yolk sac cells was first demonstrated as follows. After 10 passages of in vitro growth, murine yolk sac cells were washed from LIF and exposed to a combination of cytokines including IL-3, CSF's, and EPO at previously determined optimal concentrations for an additional three weeks in culture. At the end of the period, the stimulated yolk sac cells were prepared as blood smears and stained with Wright/Giemsa. The result of this analysis reveals the appearance of blood cells that can be identified as erythrocytes, granulocytes, megakaryocytes, and lymphocytes.

A similar study was also carried out in vivo by recovering donor cells four weeks after in vivo injection into allogeneic SCID mice. The yolk sac cells used in this study had been expanded in culture for over 20 passages. Double-staining of the spleen, bone marrow, and thymus cells of the SCID mice was performed using antibodies specific for the donor cell haplotype of $H-2^d$ and antibodies against mature blood cell markers such as B220 for B cells, CD3 and Thy-1 for T cells, and Mac-1 for macrophages. The finding confirms the in vitro study that long-term cultured yolk sac cells are capable of giving rise to mature T cells, B cells and macrophages/monocytes.

In addition to morphologic evidence of blood cell maturation from yolk sac cells, the adoptively transferred yolk sac cells were tested for functional activities in the form of specific antibody production. After the mice received an infusion of yolk sac cells, they were immunized with either lipopolysaccharide (LPS) or human serum albumin (HSA) a month later. Sera of mice were diluted serially, reacted with the two antigens, and compared with normal mouse sera as controls. LPS is a T cell-independent antigen which activates polyclonal B cells directly. The high titer of LPS specific antibodies in the sera of yolk sac cell-bearing beige nude xid mice after LPS immunization indicates the presence of functionally competent antibody producing cells, i.e., B lymphocytes and plasma cells. Additionally, HSA which is a T cell dependent antigen elicited a weaker yet detectable specific antibody production in mice. Since the anti-HSA antibody response requires T cell help which, in turn, is first activated by antigen-presenting cells such as macrophages, this result provides evidence for the presence of mature and functional T cells, B cells, and macrophages which co-operate and interact in the generation of antibodies. As a corollary, this also suggests that other T cell and macrophage-mediated functions such as cytotoxicity, lymphokine and cytokine secretion, phagocytosis, antigen processing and presentation may all develop from the transferred yolk sac stem cells.

The in vivo transfer of yolk sac cells also repopulated the spleens of mice whose hematopoietic system had been previously destroyed by chemical ablation or lethal doses of irradiation. This resembles situations in which a patient's lymphohematopoietic system is deficient due to a genetic disorder or an acquired viral infection, or a patient's system is intentionally destroyed by chemotherapy or radiotherapy in order to eradicate tumor cells in the bone marrow. The administration of yolk sac cells induced colony forming units-spleen (CFU-S) in lethally-irradiated or chemo-ablated mice whose spleens, otherwise, frequently exhibited a necrotic appearance. On the other hand, expansion of the yolk sac cells over a period of time in vivo supported repopulation and restoration of spleens completely normal in appearance. Further, the yolk sac cell-treated mice experienced a prolongation of survival time when compared with the untreated control group. Therefore, long-term cultured yolk sac cells may be useful in a variety of settings in which bone marrow reconstitution can be applied as an effective means of therapy.

Transplantation of murine yolk sac cells into allogeneic fetuses in utero and xenogeneic new born animals did not induce graft rejection reactions. The yolk sac cells persisted in vivo and established hematopoietic chimerism in the spleen, liver, and peripheral blood of the host. Thus, yolk sac cells may be useful as universal donor cells in various mammalian species, including humans.

5.4. USES OF YOLK SAC STEM CELLS

The absence of MHC antigen expression by yolk sac stem cells provides for a source of donor cells for in vivo transplantation and reconstitution therapy. The cells may be used immediately after isolation from the yolk sac or after long-term expansion in vitro, in order to procure larger numbers for more effective doses. Introduction of exogenous genes into the yolk sac cells may be achieved by conventional methods, including but not limited to transfection by calcium phosphate precipitation or electroporation or lipofection, and transduction with viral vectors. Alternatively, transgenic animals may be produced by microinjection of an exogenous gene into fertilized eggs and yolk sac cells obtained during early embryogenesis. Long-term cultured cells may be used as a mixed population or progenitors can be pre-selected based on the primitive phenotype of CD34⁻, MHC class I⁻ and class II⁻, or by limiting dilution cloning, prior to in vivo use.

The endothelial properties of the yolk sac cells provide for additional uses. For example, the yolk sac cells may be used for re-endothelization, vascular prosthesis and induction of angiogenesis. In addition, they may be used as vascular grafts, including grafts which secrete tissue plasminogen activator, low density lipoprotein receptor, apolipid protein A, or other biologically active substances. Such cells may also be used for constructing artificial organs, or as endothelial mini-organs for gene therapy and immune modification.

5.4.1. HUMAN YOLK SAC CELLS IN MICE

Human yolk sac cells may be obtained, grown in vitro and transferred into immunodeficient or immunocompromised mice. Such mice contain a human hematopoietic system which may be used for the study of human blood cell development in vivo, the identification of novel hematopoietic growth and differentiation factors, the production of antigen-specific human monoclonal antibodies, and testing for cytotoxic and/or inhibitory compounds that affect various stages of blood cell formation as well as anti-cancer drugs. Such a chimeric mouse referred to as Humato-Mouse™ herein is superior to the conventional SCID/Hu mouse model involving reconstitution of mice with human bone marrow stem cells because HumatoMouse™ permits studies in the delineation of the earliest events in hematopoiesis. Furthermore, yolk sac cells may be implanted in utero into normal mouse fetuses for engraftment of human blood cells in a normal mouse environment. Such yolk sac cells may be transfected with a drug-resistance gene so as to allow subsequent selective ablation of only the host cells using the corresponding drug.

It has been observed that SCID mice are not totally immunodeficient and that a small amount of restoration of immune function is correlated with the age of the mice. SCID mice possess detectable natural killer cell and macrophage activities. A small percentage of mice even re-acquire T and B cell function as they mature. Thus, conventional SCID mice may not be the most appropriate hosts for the construction of the HumatoMouse™ as their immune function may interfere with the analysis of the donor yolk sac cells. The steel mice possess a mutation at the steel locus which encodes SCF, a ligand for the proto-oncogene c-kit cell surface receptor. Mouse fetuses that are homozygous for this mutation live only to about day 15 of gestation before they are aborted due to the absence of a hematopoietic system and blood cell formation. Hence, human yolk sac cells may be injected into the developing homozygous fetuses in utero prior to abortion, e.g., at day 8, to reconstitute their hematopoietic function. The resulting neonates should have a fully humanized system with no contribution by the host as they would not normally have lived to birth.

Studies described herein demonstrate that cultured yolk sac cells can develop into mature blood cells in vivo, suggesting that the cells secrete the necessary growth and differentiation factors for supporting their own development. A further improvement of the Humatomouse™ model includes the introduction of human growth and differentiation factor genes in the mice. In the event that certain of the critical cytokines for human blood cell formation are species-specific, such as SCF, and mouse molecules do not act effectively to promote growth and differentiation of human cells, transgenic SCID or steel mice may be constructed to result in endogenous production of human cytokines of interest such as IL-3, CSF's, and SCF. Alternatively, human yolk sac cells may be transfected with murine receptor genes. The subsequent transfer of human yolk sac cells to these mice should give rise to a more complete and efficient human hematopoietic system in mice.

5.4.2. TRANSPLANTATION USING YOLK SAC CELLS

The repeated transfer of high doses of long-term cultured mouse yolk sac cells into a foreign species, i.e. sheep, has shown that the cells persist in vivo, differentiate into mature lymphocytes, and do not mediate graft-versus-host disease. Although the mature donor mouse cells eventually express MHC antigens in vivo, the donor cells are present in detectable quantities in the peripheral blood of the xenogeneic host. The absence of graft rejection (host-versus-graft) and graft-versus-host reactions may be attributed to the primitive nature of the yolk sac cells, particularly the lack of MHC antigen expression, allowing the cells and the host immune system to "learn" each other as self prior to MHC expression and thus, induce a state of specific tolerance.

Xenogeneic transplants of solid organs have been carried out in humans in situations where there is a shortage of HLA-matched organs. With respect to xenogeneic transplant of primitive hematopoietic stem cells, yolk sac cells may be used to reconstitute the hematopoietic system of any mammalian species, for example, in a human patient with HIV infection. Since non-human T cells cannot be infected by human HIV, this approach may serve as a means of limiting HIV infection in humans. Yolk sac cells may also be transfected with genes which are designed to disrupt HIV gene sequences involved in HIV replication prior to in vivo administration. Such exogenously introduced genes may encode anti-sense RNA or ribozyme molecules that specifically interfere with HIV replication (Han et al., 1991, Proc. Natl. Acad. Sci. USA 88:4313–4317). Further, the induction of tolerance by the transfer of xenogeneic yolk sac cells may allow subsequent transplantation of solid organs, including but not limited to heart, liver and kidney from donor animals sharing the same genetic makeup of the yolk sac donors. This raises the possibility of using MHC-mismatched yolk sac cells not only for reconstitution purposes, but also as first step tolerogens for inducing specific tolerance in a recipient for subsequent organ transplants.

In addition, this form of yolk sac cell transplantation may be applied in situations where a genetic defect has been discovered with a fetus. Human or other mammalian yolk sac cells carrying a normal wild type gene or an exogenously introduced functional gene may be injected into the developing fetus in a routine procedure similar to that of amniocentesis in utero. The genetic disorders for which this approach may be applicable include, but are not limited to, sickle cell anemia, thalassemia, and adenosine deaminase deficiency. Alternatively, yolk sac cells may be used in settings where a pregnant mother is diagnosed to carry HIV, and reconstitution of the fetus with yolk sac cells may prevent viral infection of the fetus.

The ability of yolk sac cells to grow in xenogeneic animals with no irradiation or chemical treatment allows for large scale production of human hematopoietic cells and their secreted factors in vivo. Human yolk sac cells may be injected in a large farm animal, the blood collected, and large quantities of human proteins or cells such as red blood cells, lymphocytes, granulocytes, platelets, monoclonal antibodies and cytokines purified for clinical use.

5.5. BONE MARROW REPLACEMENT THERAPY IN HUMANS

A protocol for the replacement of bone marrow cells in human patients requiring bone marrow transplantation may be devised using cultured human or xenogeneic yolk sac cells. Yolk sac cells obtained from human primary yolk sac at day 10 or shortly thereafter or from human secondary yolk sac at day 14–28 of gestation may be isolated using the procedures described in Example 7, infra, expanded in culture, and cryogenically preserved as donor cells for the transplant.

Ablation of recipient patient bone marrow cells may not be required, but if it is used, it can be accomplished by standard total body irradiation (Kim, et al., Radiology, 122:523, 1977) or by chemotherapy with a variety of commonly used compounds including, but not limited to Busulfan (Tutschka, et al., Blood, 70:1382–1388, 1987), following the conventional methods. Yolk sac cells can be introduced into the recipient, using similar methods for bone marrow cells. Prior to in vivo transfer, yolk sac cells may be transformed with a drug-resistance gene, such as the methotrexate resistance gene. This allows the subsequent use of high doses of the corresponding chemotherapeutic drug to eradicate the less resistant host cells in a patient, without damage to the transferred yolk sac cells. Post-operative care would be the same as with transplantation using bone marrow cells from a donor.

High doses of yolk sac cells obtained from allogeneic or xenogeneic sources may be continuous infused into a bone marrow transplant recipient in the absence of prior chemotherapy or radiotherapy. This presents a novel approach to bone marrow transplantation without immunosuppressing the recipient.

5.6. IDENTIFICATION OF NEW MARKERS ON YOLK SAC CELLS

The yolk sac cells described herein display a very primitive phenotype and do not express many of the known hematopoietic stem cell markers tested. It is possible that yolk sac cells express other early markers which have not yet been identified. If so, previous failure in identifying these unique molecules might be due to their decreased expression in more mature cells or even stem cells after migration to other sites out of the yolk sac. Therefore, yolk sac cells may be used to generate antibodies against their cell surface antigens in order to identify and characterize such unknown markers.

Also within the scope of the invention is the production of polyclonal and monoclonal antibodies which recognize novel antigenic markers expressed by yolk sac cells. Various procedures known in the art may be used for the production of antibodies to yolk sac cells. For the production of antibodies, various host animals can be immunized by injection with viable yolk sac cells, fixed cells or membrane preparations, including but not limited to rabbits, hamsters, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peotides, oil emulsions, keyhole limpet hemocyanin, dinitrophenol, and potentially useful human adjuvants such as BCG (bacille Calmette-Guerin) and *Corynebacterium parvum*.

Monoclonal antibodies to novel antigens on yolk sac cells may be prepared by using any technique which provides for the production of antibody molecules by continuous cell lines in culture. These include but are not limited to the hybridoma technique originally described by Kohler and Milstein (1975, Nature 256, 495–497), and the more recent human B-cell hybridoma technique (Kosbor et al., 1983, Immunology Today 4:72; Cote et al., 1983, Proc. Natl. Acad. Sci. 80:2026–2030) and the EBV-hybridoma technique (Cole et al., 1985, Monoclonal Antibodies and Cancer Therapy, Alan R. Liss, Inc., pp. 77–96). Techniques developed for the production of "chimeric antibodies" by splicing the genes from a mouse antibody molecule of appropriate antigen specificity together with genes from a human antibody molecule can be used (e.g., Morrison et al., 1984, Proc. Natl. Acad. Sci., 81:6851–6855; Neuberger et al., 1984, Nature, 312:604–608; Takeda et al., 1985, Nature 314:452–454). In addition, techniques described for the production of single chain antibodies (U.S. Pat. No. 4,946,778) can be adapted to produce single chain antibodies.

Syngeneic, allogeneic, and xenogeneic hosts may be used for injection of yolk sac cells which can be prepared in viable form, or in fixed form, or as extracted membrane fragments. Monoclonal antibodies can be screened differentially by selective binding to yolk sac cells, but not to mature macrophages, granulocytes, T, and B cells.

Antibody fragments which contain the binding site of the molecule may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

6. EXAMPLE

GENERATION OF MURINE YOLK SAC STEM CELLS FOR IN VIVO HEMATOPOIETIC RECONSTITUTION

6.1. MATERIALS AND METHODS

6.1.1. ANIMALS

BALB/c, C57BL/6, beige nude X-linked immunodeficient (BNX), and C3H/SCID mice were purchased from Jackson Laboratories (Bar Harbor, Me.) and kept in the animal facility of Edison Animal Biotechnology Center.

6.1.2. ISOLATION OF THE EMBRYONIC YOLK SAC

6.1.2.1. SURGICAL EXCISION

On day 7 of gestation (day of plug was counted as day 0), female mice were sacrificed by cervical dislocation, and uteri containing embryos were placed in petri dishes with Dulbecco's Phosphate Buffered Saline (PBS) plus penicillin and streptomycin antibiotics (final concentration :1000 units potassium penicillin G and 1000 µg streptomycin sulfate/ml).

Under a laminar air-flow bench, each uterine segment containing an embryo was aseptically removed by dissection with the aid of a dissecting microscope. Each embryo surrounded by decidua capsularis was transferred to another petri dish containing PBS plus penicillin-streptomycin. The decidua capsularis was opened with watchmaker's forceps and each embryo transferred into an individual petri dish where yolk sac tissue was excised from the amnion, placenta, embryo, and Reichert's membrane in 0.02% EDTA in PBS at 4° C. for 15–30 minutes. Alternatively, the yolk sac tissue was digested by a trypsin-collagenase solution, although the use of EDTA is believed to be a gentler method for the preservation of cell viability. The yolk sac cells in single cell suspension were then washed in PBS before culturing.

6.1.2.2. BLASTOCYST INDUCTION

Alternatively, yolk sac cells were also generated using an in vitro blastocyst induction method in which murine embryos were recovered 3.5 days after the detection of a vaginal plug. At this point the developing embryos were at the morula or blastocyst stage of development. Both morula and blastocyst stage embryos had been utilized in the studies with no apparent difference in outcome. These very early stage embryos were chosen as the starting material because they represented stages of embryonic development where only limited lineage commitment had occurred. For example, the initial steps of lineage commitment occur in the morula. The relative position of individual cells within the morula has been shown to determine whether they will become trophoblasts or ICM cells. Trophoblast cells are not directly involved in the formation of the embryo, instead their role is primarily one of providing nutritional and structural support. The cells of the ICM are the predecessors of the embryo.

Pregnant mice at 3.5 days beyond detection of the vaginal plug were sacrificed by cervical dislocation. Their uteri were surgically removed and placed in a 100 mm dish containing 20 mls of unsupplemented alpha medium (Sigma) prewarmed to 37° C. The uteri were washed by transferring them through a series of three additional dishes containing 20 mls of prewarmed alpha medium. At transfer, each uterine segment was agitated to reduce the level of maternal blood cell contamination. Washed uteri were then cannulated at one end with an 18 gauge blunt-ended needle connected to a 5 cc syringe containing complete growth medium composed of 50/50 mix of F-12 and alpha MEM media (Gibco) supplemented with 18% fetal calf serum (FCS) (Hyclone), 10% LIF-conditioned medium, 0.2 mM β-mercaptoethanol and 50 µg/ml gentamicin. The tips of a forceps were applied to the uterine tissue around the circumference of the cannula to hold the tissue in place. Medium from the syringe was then introduced into the lumen of the uterus with sufficient force to flush free the developing embryos. The uteri were flushed into an empty 35 mm dish. Embryos were then selected for use on the basis of health and stage of development as detected by examination under a dissecting microscope. Healthy 3.5 day morula or blastocysts were transferred to dishes coated with a thin layer of "MATRIGEL" (Collaborative Biomedical Products, Becton Dickinson Labware, Bedford, Mass.) and containing the inducing medium (complete medium containing 10% LIF-conditioned medium, 200 ng/ml IL-3, 20 ng/ml IL-4, 100 ng/ml IL-6, 2 u/ml EPO and 40 ng/ml SCF). "MATRIGEL" is a solubilized basement membrane preparation extracted from a mouse sarcoma. This preparation includes laminin, collagen, heparan sulfate proteoglycans, entactin, nidogen, TGF-β, FGF, tissue plasminogen activator and other growth factors. "MATRIGEL"-coated dishes were either purchased, or they were prepared by applying a thin layer of "MATRIGEL" at 4° C. to the bottom of the dish and allowed to solidify at 37° C. according to manufacturer's protocol. The size of the dish used was determined by whether the embryos would be examined individually, 15 mm well, or in groups, 20 mm well. Inducing medium was changed at 48 hr intervals. The yolk sac tissue was the outermost layer as the day 3.5 blastocysts developed in vitro. The yolk sac cells grew out onto the "MATRIGEL" surface away from the embryo as time went on. After two to three weeks, cytokine treatment was discontinued and the cultures were maintained in complete growth medium until passage. The embryonic portions were removed by fine surgical scissors prior to first passage. Eventually, the yolk sac cells would grow and completely filled the culture dish.

6.1.3. CULTURE CONDITIONS

Disaggregated yolk sac cells were grown in alpha medium (Sigma) supplemented with 18% heat-inactivated fetal calf serum, 0.2 mM β-mercaptoethanol, 50 µg/ml of gentamicin and 10% LIF conditioned medium; i.e. medium of a LIF-producing cell line, Cho LIFD, at $10^2$–$7.5 \times 10^5$ u/ml. Cells were first plated on a feeder layer of freshly isolated mouse embryonic fibroblasts previously treated with mitomycin to inhibit cell division. For long term maintenance of the yolk sac cells, they were removed from the feeder layer and grown on 0.1% gelatin coated dishes at 37° C. in 5% $CO_2$ in air. It was found that the isolated yolk sac cells could also be grown directly on gelatin or collagen coated dishes in the absence of feeder layers but in the presence of LIF, at the initiation of culture. Media were changed every other day.

6.1.4. FLOW CYTOMETRY ANALYSIS $10^6$ yolk sac cells were washed twice in cold PBS containing 0.1 BSA and sodium azide. The cell pellets were suspended in 100 µl of the same buffer containing the test antibodies at 4° C. for 30 minutes. Cells were then washed in cold PBS twice, resuspended in 0.5 ml of fixative (paraformaldehyde), and analyzed by a Fluorescence Activated Cell Sorter (Becton Dickinson).

Antibodies specific for Thy-1, Ly-1, Ly-2, Mac-1, MHC class I and class II were purchased from Boehringer Mannheim. Anti-M1/70, anti-H2$^d$ and anti-H2$^b$ antibodies were purchased from Pharmingen (San Diego, Calif.). Anti-murine c-kit (ACK-2) rat monoclonal antibody was purchased from Gibco-BRL. The use of this antibody to stain yolk sac cells required the addition of a second FITC-labeled rabbit anti-rat IgG whole molecule (Sigma). The secondary antibody was used at 1:30 dilution in PBS-BSA containing 10% normal rabbit serum at 4° C. for 30 minutes.

Expression of ac-LDL receptor by yolk sac cells was tested by incubation of cells with a fluorochrome-coupled reagent (dilac LDL) (Biomedical Technologies) for 4 hours or overnight to permit internalization. Internalization was then detected by flow cytometry or by microscopic examination using ultraviolet light excitation.

Expression of ACE by yolk sac cells was assayed by binding of a monoclonal antibody to ACE (Auerbach et al., 1982, Proc. Natl. Acad. Sci. USA 79:7891) and flow cytometry. An isotype-matched irrelevant antibody was used as control. In addition, ACE enzymatic activity was also tested by measuring the ability of yolk sac cells to cleave $^3$H-labelled tripeptide (Hip-Gly-Gly) using a standard ACE assay kit (Vector Laboratories). The activity of yolk sac cells was compared to a positive serum control, a strongly positive endothelial tumor line (endothelioma) and a negative fibroblast cell line (L929). The experiment was carried out with $2 \times 10^6$ cells except for endothelioma which was used at $1 \times 10^6$ cells. The cells were harvested with trypsin, washed twice with PBS, resuspended in PBS, and filtered through 48µ mesh Nitex. The standard vector assay kit was used according to package insert. The actual dpm value had been multiplied by 2.

6.1.5. INDUCTION OF YOLK SAC DIFFERENTIATION

BALB/c yolk sac cells were grown to approximately 50% confluency in medium containing LIF. The cells were harvested, washed and medium containing growth factors was added. Growth factors used were: LIF (100–1000 U/ml) (Genzyme), SCF (50 U/ml) (Genzyme), EPO (1–25 U/ml) (Boehringer Mannheim), IL-2 (10–200 U/ml) (Genzyme), and IL-3 (10–200 U/ml) (Genzyme) in various combinations. The medium was changed every 2 days until confluency was reached, at which time the yolk sac cells were passed 1:4 into new gelatinized 35 mm culture dishes. At day 5, and 21, cells were prepared for blood staining. Day 0, 5, and 21 cells were analyzed by flow cytometry for the appearance of differentiated blood cells.

6.1.6. HEMAGGLUTINATION ASSAY

Lipopolysaccharide (LPS) conjugated to trinitrophenol (TNP) and human serum albumin (HSA) conjugated to TNP were injected at 20 µg/mouse intraperitoneally into BNX mice and SCID mice, respectively, both of which had previously received $10^6$ long-term cultured murine yolk sac cells intraperitoneally a month earlier. A second injection of the antigens was performed one week later, animals were bled after seven days and sera assayed for the presence of specific antibodies.

A two-fold serial dilution of the mouse sera was made in microtiter plates. Sheep red blood cells (SRBC) coated with dinitrophenol (DNP) were added to each well. The plates were incubated at room temperature for one hour. The results of the assay were assessed visually. A diffused pattern of SRBC indicated a positive TNP-specific antibody response. Negative wells had a small, tight pellet of SRBC.

6.1.7. REVERSE TRANSCRIPTION-POLYMERASE CHAIN REACTION (RT-PCR)

Total RNA was isolated from long-term cultured yolk sac cells, murine myeloid leukemia cell line M1, and murine bone marrow cells using RNAzol B (Cinna Biotecx) RT-PCR was performed using reagents and protocols provided in the RT-PCR GeneAmp kit (Perkin Elmer-Cetus). Briefly, 1 µg of total RNA was reverse transcribed using random hexamers by incubating the reactions at room temperature for 10 minutes followed by 42° C. for 15 minutes, then 95° C. for 5 minutes. The reactions were diluted into PCR buffer containing the appropriate amplimers and amplified for 40 cycles using the following 3-step program: 94° C. for 30 sec, 60° C. for 30 sec, and 72° C. for 30 sec. Following PCR, one-fifth of the reaction was analyzed by agarose gel electrophoresis and visualized by ethidium bromide staining. The nucleotide sequence of the 400 bp product amplified from M1 RNA was determined to be identical to CD34 cDNA. In a subsequent experiment, this fragment was radiolabelled and used as a probe in a Southern blot of the RT-PCR reactions.

The amplimers used to amplify a 400 bp fragment of CD34 cDNA were based on the published murine CD34 cDNA sequence (Blood, 79:2288–2295, 1992):

(+)-strand 5' CTACCACGGAGACTTCTACAC 3'(SEQ ID NO:1)

(−)-strand 5' GCACTCGGAGCAGAAGATGAT 3'(SEQ ID NO:2)

The amplimers used to amplify β-actin cDNA as controls were as previously described (Genes and Development, 5:728–740, 1991).

Additionally, PCR primers designed from published sequences of murine receptor tyrosine kinases flk-1 and tek were employed in reactions with reverse transcribed RNA. RNA samples included 2 mg total yolk sac cell RNA, 2 mg total COS7 cell RNA, and 100 ng polyA$^+$ RNA isolated from an 11.5 day mouse embryo. In order to eliminate the possibility that amplified bands represented DNA contamination, yolk sac RNA was subjected to PCR without treatment with reverse transcriptase. Control PCR reactions run with COS7 cell RNA and yolk sac RNA without reverse transcriptase treatment did not show an amplified band. The flk-1 primers used were as follows:

(t)-strand 5' AgC TgT CgC TCT gTg gTT CT 3'(SEQ ID NO:3)

(−)-strand 5'Tgg ggA gag TAA AgC CTA TC 3'.(SEQ ID NO:4)

When the murine yolk sac cells were removed from LIF-containing medium and grown in alpha MEM containing 5% FBS, 10 ng/ml SCF and 2 u/ml EPO, they were tested for the expression of β globin mRNA. Total RNA was isolated by the acid phenol procedure. The first-strand cDNA reaction was performed using Moloney murine leukemia virus (Mo-MLV) reverse transcriptase (BRL) according to the manufacturer's protocol with 15 units of RNA guard and 20 pmoles of random hexamer primers (Pharmacia) in a 40-µl reaction. This reaction contained ~20 ng of total RNA, which represents approximately the equivalent of $2\times10^3$ cells. The same first-strand preparation was used for analyzing each of the genes. To control for template or other contaminations that would interfere with the PCR results, one first-strand reaction contained no RNA template and duplicates of each reaction were performed without reverse transcriptase.

PCR amplifications were performed with 2.5% of the first-strand reaction product with Taq polymerase (2.5 units) (Promega) according to the manufacturer's protocol using 50 pmoles of each of the two gene-specific amplimers in a reaction volume of 100 µl. Most PCRs were assayed at two different cycle numbers by removing one-half of the reaction volume at appropriate times during the amplification. This allowed for the control of "saturation effects" of the PCR, which made it possible to better judge quantitative differences between samples. The reactions were carried out in a Cetus thermocycler for 25–50 cycles consisting of 1' 94° C., 1' 60°–65 ° C. (depending on the melting temperature of the primer pair) 2' 72° C. with 2" increments per cycle. The specificity of the PCR product was established by comparing the size of the amplified product to the expected cDNA band, and most were hybridized with an internal oligonucleotide. As an internal standard, all cDNA samples were adjusted to yield relatively equal amplification of β-actin. The reverse transcriptase-negative control was performed in all PCR experiments which amplified contaminating DNA (genomic or otherwise) in the RNA preparation. The sensitivity of PCR reaction was estimated by titrating a known number of synthetic RNA molecules with the relevant primer sites into a first-strand reaction with RNA known to be negative for the message of interest. This technique controls for the efficiency of the first-strand synthesis as well as the amplification efficiency of the specific primer pairs used.

An aliquot of each PCR reaction was separated on agarose gels, and the DNA was blotted with 0.4 N NaOH onto Zeta probe membranes (Bio-Rad). The blots were hydrolyzed with internal oligonucleotides, unrelated to the PCR primers, specific for the respective amplification product, and washed at a final stringency of 20 mM Tris-HCl (pH 8), 100 mM NaCl, 0.6 mM EDTA, and 0.1% SDS at 2°–5° C. below the melting temperature of the probe.

The amplimers used were as follows:

(+)-strand 5' ATGGTGCACCTGACTGATGCTG 3'(SEQ ID NO:5)

(−)-STRAND 3' GGTTTAGTGGTACTTGTGAGCC 3'(SEQ ID NO:6)

6.2. RESULTS

6.2.1. ISOLATION OF MURINE YOLK SAC CELLS

In the mouse, the yolk sac is fully formed by day 7 and blood island formation appears by day 8.5 of gestation. Therefore, in order to isolate relatively homogeneous and undifferentiated yolk sac cells, mouse embryos were surgically removed prior to visible blood island formation, preferably at day 7 of gestation. The yolk sac region of the embryos was separated by excision, and the external surface of the yolk sac was immersed in a trypsin-collagenase solution or cold EDTA which caused the detachment of the yolk sac cells from the membrane into a single cell suspension. When the physical appearance of yolk sac cells obtained from day 7 (FIG. 1A) and day 8.5 (FIG. 1B) embryos following cold EDTA immersion prior to flow cytometry was compared by flow cytometry analysis, freshly isolated day 7 cells clearly displayed a much more uniform cell shape and cell size than the day 8.5 cells, suggesting that yolk sac cells were a homogeneous population at day 7 (FIG. 2A) but by day 8.5 (FIG. 2B), differentiative activities had already occurred to generate a mixed population of cells in the yolk sac. In addition, yolk sac cells derived from 7 day-old embryos by the surgical method and yolk sac cells derived by the blastocyst induction method appeared identical in morphology, phenotype and growth characteristics. Thus, these cells were used interchangeably for the experiments described infra.

6.2.2. CELL SURFACE PHENOTYPE OF YOLK SAC CELLS

The freshly isolated yolk sac cells from day 7 mouse embryos were immediately examined for their cell surface expression of a number of known markers by reactivity with monoclonal antibodies. Such uncultured yolk sac cells did not express Thy-1 (FIG. 3A), MHC class II (FIG. 3B) and class I (FIG. 3C) antigens. This phenotype was retained during long-term expansion, and the cultured murine yolk sac cells were also shown to be c-kit+ (FIG. 4). The absence of MHC antigen expression at this stage is significant in that the likelihood of rejection of these cells by a genetically disparate host upon in vivo transfer is greatly reduced. Further, the lack of Thy-1 expression indicates that the yolk sac cells of the invention represent an earlier cell population in ontogeny than the Thy-1+ hematopoietic stem cells found in bone marrow, thus should contain a pluripotent population that is less committed to any specific cell lineages. In further support of this possibility, the yolk sac cells were also shown to be CD34−. Although the yolk sac cells isolated in the manner described herein were once believed to be CD34+, subsequent analysis using the polymerase chain reactions (PCR) did not detect any expression of CD34 RNA in these cells (FIG. 5). PCR is much more specific and sensitive than the antibody techniques used in earlier studies.

In addition, the cultured yolk sac cells also expressed phenotypic markers characteristic of the endothelial cell lineage. For example, when the cells were incubated with ac-LDL, they were able to internalize LDL (FIG. 6 A and B). Additionally, the yolk sac cells were stained by antibodies directed to VCAM (FIG. 7), MECA-99 which were known endothelial markers. On the other hand, they were negative for staining with antibodies directed to macrophage markers such as F4/80 and Mac-1. Furthermore, the cells also expressed ACE as assayed by antibody staining and its enzymatic activity in cleaving radiolabelled tripeptides (Table I).

TABLE I

| Cells Assayed | DPM | relative to control (corrected for background) |
| --- | --- | --- |
| (total counts) | 186,863 | |
| serum standard | 43,847 | |
| blank | 5,971 | |
| serum standard (corrected) | 37,876 | 100.0% |
| Endothelioma | 112,253 | 281.2% |
| L929 fibroblasts | 6,614 | 1.7% |
| Yolk sac cells (sample 1) | 71,151 | 172.1% |
| Yolk sac cells (sample 2) | 66,794 | 160.6% |
| Blank | 5,971 | 0 |

When the murine yolk sac cells were examined for the expression of two additional endothelial markers by RT-PCR, a specific band was detected for flk-1 and tek (FIG. 8 Lane 1 and FIG. 9 Lane 1, respectively). Additionally, when the cells were grown in the presence of hematopoietic growth factors such as SCF and EPO, adult globin message was induced (FIG. 10).

Taken together, the results indicate that the yolk sac stem cells possess both hematopoietic and endothelial cell phenotypic characteristics.

6.2.3. LONG-TERM MAINTENANCE OF YOLK SAC CELLS

The yolk sac cells were established in long-term cultures in the presence of leukemia inhibitory factor (LIF) without a feeder layer. The cells expanded in number, having a doubling time of about 18 hours. Such cultured cells have been grown in vitro in the presence of LIF for over 55 passages covering a period of time over 1 year in continuous culture.

The long-term cultured cells retained their original cell surface phenotype. Further, such cells continued to be pluripotent as evidenced by their ability to give rise to blood cells in vitro and in vivo, infra. The cells with the original phenotype in long-term cultures may also be cloned by cell sorting or by repeated limiting dilution cloning.

6.2.4. ENDOTHELIAL GROWTH CHARACTERISTICS OF YOLK SAC STEM CELLS

When the murine yolk sac cultures were allowed to remain at high cell density in vitro, multiple layers of cells piled on top of each other. After a period of time, cells began to arrange themselves in an organized fashion and eventually proceeded to form what appeared to be a rudimentary capillary-like network throughout the surface of the culture dish. At various points along their length, such tubular structures bulged out and frequently appeared to contain unique populations of cells which were tightly packed together and displayed a rust-like coloration under bright field illumination (FIG. 11). In addition, the cultures released cells into the supernatant, and these cells resembled blood cells when examined with standard hematological stains, e.g. Wright-Giemsa.

These observed in vitro events of yolk sac cells were very similar to those believed to occur in the yolk sac in vivo. In vivo, it is believed that blood islands consist of an endothelial cell outer layer surrounding an inner population of blood forming cells. As individual blood islands develop, their endothelial outer layers fuse with neighboring blood islands, forming a rudimentary vascular network, and the inner cells of the blood island mature to become the functional blood cells of the early embryo.

6.2.5. DIFFERENTIATION OF YOLK SAC CELLS IN VITRO

After one month of in vitro culture in the presence of LIF, the yolk sac cells were tested for their ability to differentiate into mature blood cells of all lineages in response to various known hematopoietic growth factors including IL-3, IL-2, and EPO, upon the removal of LIF. When cultured in IL-3 and EPO, the appearance of red blood cells was readily detectable in the yolk sac cultures. In response to CSF's and IL-3, the yolk sac cells matured into megakaryocytes and granulocytes. FIG. 12 A–D is a blood stain of a yolk sac culture grown in the presence of a combination of cytokines and the appearance of various blood cell lineages can be identified. In addition, the expression of various leukocyte surface markers by these cells became detectable, including CD45, LFA, MAC-1, Ly-1 and Ly-2. Hence, yolk sac cells could be expanded in number with minimal differentiation, and stimulated to develop into mature blood cells upon exposure to certain specific growth factors at a later stage.

6.2.6. DIFFERENTIATION OF YOLK SAC CELLS IN VIVO

A long-term culture of yolk sac cells of BALB/c origin was injected into allogeneic C3H/SCID mice after 22 passages in vitro. Four weeks later, spleens and livers of the treated animals were analyzed for the presence of donor cells by monoclonal antibodies.

The donor cells were identified by antibodies specific for the donor H-$2^d$ haplotype. Double-staining experiments utilizing two antibodies further demonstrated that certain subpopulations of the donor cells expressed CD3, Thy-1, B220 and M1/70 (FIG. 13A–G). Therefore, these results indicated that the long-term cultured mouse yolk sac cells were capable of differentiating naturally in vivo into T cells, B cells and macrophages.

6.2.7. GENERATION OF IMMUNOCOMPETENT CELLS BY YOLK SAC CELLS IN VIVO

In order to examine whether the yolk sac cells could give rise to functionally mature blood cells, a long-term cultured yolk sac line was transferred in vivo into allogeneic SCID or BNX mice, and tested for specific antibody production. When the BNX mice received yolk sac cells and were subsequently immunized with LPS a month later, specific antibody titers were detected in the sera (FIG. 14 A and B). As LPS is a polyclonal B cell activating agent, this result shows the presence of functionally active antibody-producing B cells. Additionally, when SCID mice were injected with yolk sac cells followed by HSA immunization, which is a T cell dependent antigen, an antibody response was again detectable, suggesting that long-term cultured yolk sac cells could differentiate to become immunocompetent T and B cells in vivo.

6.2.8. YOLK SAC CELLS REPOPULATE CHEMO-ABLATED MOUSE SPLEENS

Certain classes of chemotherapeutic drugs are effective, and have been used, as ablative agents for bone-marrow in bone-marrow transplantation procedures (Floersheim and Ruszkiewicz, 1969, Nature 222:854). One of the most effective agents used to replace whole body irradiation in bone-marrow transplantation procedures is the drug Busulfan (Tutschka et al., 1987, Blood 70:1382). Through careful titration of the dose of Busulfan and the use of inbred lines of mice (C57BL/6) of a defined age and weight (3–4 weeks of age), doses of Busulfan have been determined which fully ablate the bone marrow of these mice but do not directly kill them. These doses of Busulfan result in the eventual death of the treated mice between 11 and 14 days if they do not receive transplanted bone-marrow. This dose is 65 mg of Busulfan/g of body weight administered in a single dose by I.P. injection. When C57BL/6 mice were treated with this dose of Busulfan and then received an I.P. injection of $10^6$ syngeneic long-term cultured yolk sac cells 24 hrs. following Busulfan treatment, the transplant recipients revealed spleen repopulation at day 7 and 14 post Busulfan treatment (FIG. 15 A–C). On day 7, spleen colony formation within the recipient was observed, indicative of the initial stages of splenic repopulation by the transplant. Additionally, comparison at day 12 post treatment, of the spleens of control Busulfan treated mice not receiving yolk sac transplants and those animals receiving transplants showed a marked difference in splenic viability. While the spleens of control animals were dark, almost black color, and appeared necrotic, the spleens of transplant recipients displayed a normal red/pink color, and appeared normal and healthy. Further, the survival time of the yolk sac cell-treated mice was extended to between 18 and 20 days.

6.2.9. IN UTERO ADMINISTRATION OF YOLK SAC CELLS RESULTS IN TISSUE CHIMERISM

A long-term cultured yolk sac cell line was tested for its ability to survive in an allogeneic host. 10,000–50,000 BALB/c yolk sac cells after 13–20 passages in vitro were injected in utero in day 8 embryos of C57BL/6 mice. At birth, the spleens and livers of the neonates were harvested and analyzed for the presence of donor cells.

Since the donor cells were of the H-$2^d$ haplotype, a monoclonal antibody specific for H-$2^d$ antigens was used to identify the donor cells by flow cytometry analysis. FIG. 16A–F presents the results from two neonates examined and it clearly shows that donor cells were present in both the liver and spleen of the recipient mice in substantial numbers. Therefore, in utero administration of yolk sac cells into MHC-mismatched mice resulted in tissue chimerism, and survival and homing of the cells to the lymphohematopoietic organs. Tissue chimerism was retained when the mouse tissues were examined even one month after birth.

6.2.10. XENOGENEIC TRANSPLANTATION OF YOLK SAC CELLS RESULTS IN LONG-TERM PERSISTENCE OF CELLS IN VIVO

In order to test the feasibility of using yolk sac cells in xenogeneic transplantation and reconstitution, long-term cultured BALB/c yolk sac cells were injected into a newborn Hampshire sheep and a Nubian goat. The sheep received $40 \times 10^6$ murine yolk sac cells intravenously at day 3 after birth and the goat received the same cell dose at day 7 after birth. Four days later, both animals received a second dose of $200 \times 10^6$ cells. After four additional days, a final injection of $60 \times 10^6$ cells was given, the peripheral blood mononuclear cells were harvested for antibody staining and flow cytometry analysis about one and a half months later.

FIG. 17A–F demonstrates that a substantial number of blood cells obtained from the sheep were reactive with anti-H-$2^d$ antibody. While there were lower numbers of donors in the peripheral blood of the goat, donor cells were nonetheless detectable. In addition, cells expressing the murine T cell marker Ly-1 were also present from both animals. However, neither animal had cells that were positive for the murine macrophage marker Mac-1, consistent with the fact that macrophages are not normally present in the peripheral blood.

The results of this experiment are revealing in a number of ways. It illustrates the possibility of xenogeneic reconstitution using murine yolk sac cells. Neither animal was pre-treated with irradiation or cytotoxic drug. The high cell doses and the repetitive injections did not induce graft rejection. Both animals also appeared normal and healthy, having no indication of graft versus host reaction. The consistent finding of a higher number of donor cells recoverable from the sheep than the goat may be a result of the goat being of an older age before receiving the first cell injection. The younger age of the sheep when it was given the first cell dose might have resulted in a more efficient induction of tolerance. However, there was still acceptance of the donor cells in the goat in the absence of any prior immunosuppressive treatment. If induction of tolerance is the mechanism underlying this observation, this further suggests that the tolerized hosts may also accept other solid organs including the heart, liver and kidney from xenogeneic donors sharing the same haplotype of the original donors. Finally, the expression of a T cell marker indicates normal differentiation and maturation in vivo, and the absence of macrophages in the peripheral blood suggests the appropriate homing of the right cell lineages in the host upon intravenous administration of yolk sac cells.

7. EXAMPLE

GENERATION AND CHARACTERIZATION OF HUMAN YOLK SAC STEM CELLS

7.1. MATERIALS AND METHODS

7.1.1. ISOLATION OF THE EMBRYONIC YOLK SAC

Tissues were recovered from aborted human fetuses at approximately 4–8 weeks of gestation. The optimal isolation period was approximately 4–6 weeks. At this time, a well defined yolk sac was present but an extensive vascular network had not yet formed, i.e., blood cells had not yet begun to migrate into the embryo in a prominent way. Although it would be possible to isolate yolk sac tissue from earlier stages of fetal development, abortions are rarely performed before the fourth week in the United States. Following careful examination, prospective yolk sac samples were identified and isolated away from other fetal tissue fragments on the basis of their unique morphology. The unique morphology was seen as a bulbous structure on the end of a fairly long tether of tissue connecting the yolk sac with the embryo.

Once recovered, prospective yolk sac samples were partially disaggregated in a small volume of complete growth medium, using the scissor-like action of two opposing 30 gauge needles, and transferred to a collagen S-(type-1) coated (Boehringer Mannheim) well of a 24-well plate. A sterile trypsin/collagenase solution (0.25% and 600 U/ml, respectively) was added for further cell dispersal and early passaging, while the cultures were maintained on a collagen substrate. When the cultures became established, they were grown on gelatin-coated dishes (0.1%) and dissociated through the use of a 0.25% trypsin solution for passage. Complete growth medium consisted of αMEM supplemented with 18% fetal calf serum, 18% LIF-conditioned medium, 0.2 mM β-mercaptoethanol and 50 µg/ml gentamicin. This media formulation was utilized for both initial culture development, and for large scale maintenance and expansion. The cell line was subsequently cloned by limiting dilution.

7.1.2. INDUCTION OF GLOBIN EXPRESSION

A clonally-derived human yolk sac cell line was induced with cytokines and its expression of globin mRNA was examined by RT-PCR analysis. Separate cultures were grown in a common base medium consisting of F-12/IMDM (50/50) supplemented with 5% FCS, 40 µg/ml insulin, 2.1% BSA, 250 µg/ml transferrin, 2 mM L-glutamine, 27 ng/ml vitamin E, 25 µg/ml gentamicin, and 70 µM MTG which further contained various combinations of additional cytokines. IGF/FGF medium refers to base medium supplemented with 5 ng/ml FGF and 10 ng/ml Insulin-like growth factor (IGF-I). Total medium refers to IGF/FGF medium further supplemented with 10 ng/ml IL-3, 500 u/ml IL-6, 1.7 u/ml EPO and 17 ng/ml SCF. TGF-α(-LIF) medium refers to base medium supplemented with 10 ng/ml TGFα, 250 mU/ml EPO, 2 µM hemin, 2.5 µg/ml folic acid, and 5 µg/ml vitamin B12. TGFµ complete medium refers to TGFµ(-LIF) medium further supplemented with 1% LIF.

The yolk sac cells were cultured in each of the above-described conditions. The non-adherent cells in the supernatants of each of these cultures were collected and transferred to a new culture flask where the cells were grown for about 10 days. During this period, the pH of the cultures was maintained by the addition of the base medium; however, no additional cytokine was used. On the day of RT-PCR analysis, the cells in the supernatants were collected from each culture and prepared as individual samples for globin message detection.

The HEL 92.1.7 cell line was used as positive control which was known to express globin. The KG1A cell line was used as negative control. Identical reverse transcription reactions were performed with or without reverse transcriptase to serve as negative controls and to detect contaminating genomic DNA. All components, except for the sample cDNA, were premixed before dividing into each tube. The blank control consisted of a portion of the premix with no sample added. The same samples were simultaneously assayed with primers which specifically amplify actin expression as an internal control.

The samples were analyzed by RT-PCR for the expression of globin mRNA. The three sets of primers corresponded to three different human globin polypeptide chains: the α chain present in most globin isoforms (primers HUAG), the β chain present in the adult globin isoform (primers HUBG), and the γ chain present in the fetal globin isoform (HUGG). Each sample contained 50 mM KCL, 10 mM Tris-HCL, pH 8.3, 2.5 mM MgCl$_2$, 0.01% BSA, 0.01% triton X-100, 0.2 mM each dNTP, 4.5 ng each primer, and 1 unit of Amplitaq DNA polymerase in a total volume of 50 μl. The cycling conditions used an initial denaturation of 94° C., for 3 min. and a final extension at 72° C. for 7 min. 20 μl of each sample was analyzed on a 1.5% agarose gel.

The human-specific α globin (HUAG) primer sequences used were as follows:

Forward primer 5' ACA GAC TCA GAG AGA ACC CAC CAT 3' (SEQ ID NO:7)

Reverse primer 5' GCT TAA CGG TAT TTG GAG GTC AGC 3'. (SEQ ID NO:8)

The human-specific β globin (HUBG) primer sequences used were as follows:

Forward primer 5' CGT GGA TGA AGT TGG TGG TGAG 3' (SEQ ID NO:9)

Reverse primer 5' ATT AGC CAC ACC AGC CAC CAC T 3'. (SEQ ID NO:10)

The human-specific γ globin (HUGG) primer sequences used were as follows:

Forward primer 5' GGG CAA GGT GAA TGT GGA AGA T 3' (SEQ ID NO:11)

Reverse primer 5' TGG TAT CTG GAG GAC AGG GCA C 3'. (SEQ ID NO;12)

7.2. RESULTS

Human yolk sac cells were established and grown in continuous culture for about one year. Originally, the growth characteristics of the human cells looked strictly endothelial cells by morphology. When the cultured human cells were maintained at high cell density on plastic, they did not form a capillary-like network as described for the murine yolk sac cells in Section 6.2.4, supra. However, when the human yolk sac cells were grown on "MATRIGEL" (Collaborative Biomedical), they were able to form a capillary-like network whose interior was frequently 'dotted' with clusters of tightly packed, rust-colored cells. In fact, when the cells were plated on a dish, only half of which was coated with "MATRIGEL", the cells on the untreated side formed a confluent monolayer, while the cells grown on "MATRIGEL" formed tubular structures characteristic of endothelial cells (FIG. 18). In addition, as was true with the murine cultures, the cultures also released cells into the media which when examined appropriately displayed characteristics similar to those of blood cells (FIG. 19). In a repeat of the initial experiment using dishes partially coated with "MATRIGEL", the parent culture and three independent clonal cell lines derived from the parent culture by limiting dilution cloning produced identical tubular structures, and released cells into the supernatant that resembled mature cells by standard blood staining techniques.

Subsequent experiments have shown that basic fibroblast growth factor (bFGF) (Collaborative Biomedical), a "MATRIGEL" component might play an important role in promoting the development of tubular structures. Human yolk sac cell cultures grown on plastic in the presence of bFGF at 10 ng/ml formed structures similar to those grown on "MATRIGEL". In addition to bFGF, the presence of other "MATRIGEL" components, might be required to completely reproduce the effect with cells grown on plastic. It is possible that the plastic surface itself is not conducive for the desired effect and that perhaps collagen or some other more dynamic and interactive surface is required to achieve the full "MATRIGEL" effect. Thus, the human yolk sac cells are similar to the murine cells described in Example 6, supra in both morphology and growth behavior, they are capable of giving rise to both hematopoietic cells and endothelial cells.

With respect to their phenotypic characteristics, the human yolk sac cells were shown to be HLA-DR$^-$, HLA-DQ$^-$, and CD34$^-$ as stained by antibodies (Caltag Laboratories, San Francisco, Calif.). When the cells were stained with an antibody to HLA-A, B, C epitopes, >95% of the cells did not react with the antibody (FIG. 20A and B). While most of the human cells were Thy-1$^-$ a small population expressed the Thy-1 antigen (FIG. 21).

FIG. 22 shows that when a human yolk sac clone was induced with various cytokines, the cells expressed α and γ globin mRNA. On the other hand, the same cells grown in the absence of such cytokines did not produce any detectable globin message. Thus, the human yolk sac cells were capable of differentiating into blood cells upon exposure to cytokines.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A cellular composition comprising a substantially homogeneous population of cultured murine stem cells displaying a phenotype of CD34⁻, MHC Class I⁻ and MHC Class II⁻ which are capable of giving rise to blood cells.

2. A cellular composition comprising a substantially homogeneous population of cultured murine yolk sac stem cells displaying a phenotype of CD34⁻, MHC class I⁻ and MHC class II⁻ which are capable of giving rise to blood cells.

3. A method of preparing a cellular composition of murine yolk sac stem cells comprising:
   (a) excising a yolk sac from a murine embryo;
   (b) detaching murine yolk sac stem cells from yolk sac membrane; and
   (c) collecting a substantially homogeneous population of murine yolk sac stem cells displaying a phenotype of CD34⁻, MHC class I⁻ and MHC class II⁻ which are capable of giving rise to blood cells.

4. A method of preparing a cellular composition of murine yolk sac stem cells comprising:
   (a) isolating a blastocyst or morula from a murine animal;
   (b) culturing the blastocyst or morula on a substratum containing a basement membrane preparation; and
   (c) collecting a substantially homogeneous population of murine yolk sac stem cells displaying a phenotype of CD34⁻, MHC class I⁻ and MHC class II⁻ which are capable of giving rise to blood cells.

5. A method of expanding a cellular composition of murine yolk sac stem cells comprising culturing, in the presence of an agent which suppresses cellular differentiation, a substantially homogeneous population of murine yolk sac stem cells displaying a phenotype of CD34⁻, MHC class I⁻ and MHC class II⁻ which are capable of giving rise to blood cells.

6. A method of producing blood cells in vitro, comprising culturing, in the presence of a growth factor, a substantially homogeneous population of murine yolk sac stem cells displaying a phenotype of CD34⁻, MHC class I⁻ and MHC class II⁻ which are capable of giving rise to blood cells.

7. The method of claim 6 wherein the growth factor is EPO, IL-2, IL-3, G-CSF, M-CSF, GM-CSF, or a combination thereof.

8. A cellular composition comprising a substantially homogeneous population of cultured murine stem cells displaying a phenotype of CD34⁻, MHC class I⁻ and MHC class II⁻ which are capable of forming tubular structures.

9. A cellular composition comprising a substantially homogeneous population of cultured murine yolk sac stem cells displaying a phenotype of CD34⁻, MHC class I⁻ and MHC class II⁻ which are capable of forming tubular structures.

10. The composition of claim 2 or 9 wherein the yolk sac stem cells are isolated from a yolk sac prior to blood island formation.

11. The composition of claim 2 or 9 wherein the yolk sac stem cells are isolated from a mouse yolk sac at day 7 of gestation.

12. A method of preparing a cellular composition of murine yolk sac stem cells comprising:
   (a) excising a yolk sac from a murine embryo;
   (b) detaching murine yolk sac stem cells from yolk sac membrane; and
   (c) collecting a substantially homogeneous population of murine yolk sac stem cells displaying a phenotype of CD34⁻, MHC class I⁻ and MHC class II⁻ which are capable of forming tubular structures.

13. A method of preparing a cellular composition of murine yolk sac stem cells comprising:
   (a) isolating a blastocyst or morula from a murine animal;
   (b) culturing the blastocyst or morula on a substratum containing a basement membrane preparation; and
   (c) collecting a substantially homogeneous population of murine yolk sac stem cell displaying a phenotype of CD34⁻, MHC class I⁻ and MHC class II⁻ which are capable of forming tubular structures.

14. A method of expanding a cellular composition of murine yolk sac stem cells comprising culturing, in the presence of an agent which suppresses cellular differentiation, a substantially homogeneous population of murine yolk sac stem cells displaying a phenotype of CD34⁻, MHC class I⁻ and MHC class II⁻ which are capable of forming tubular structures.

15. The method of claim 5 or 14 wherein the agent is leukemia inhibitory factor.

16. The method of claim 8 or 14 wherein the agent is stem cell factor.

17. A method of producing endothelial cells in vitro, comprising culturing, in the presence of a growth factor, a substantially homogeneous population of murine yolk sac stem cells displaying a phenotype of CD34⁻, MHC class I⁻ and MHC class II⁻ which are capable of forming tubular structures.

18. The method of claim 17 wherein the growth factor is basic fibroblast growth factor.

19. A cellular composition comprising a substantially homogeneous population of cultured human stem cells displaying a phenotype of CD34⁻, MHC class I⁻ and MHC class II⁻ which are capable of giving rise to blood cells.

20. A cellular composition comprising a substantially homogeneous population of cultured human stem cells displaying a phenotype of CD34⁻, MHC class I⁻ and MHC class II⁻ which are capable of forming tubular structures.

21. A cellular composition comprising a substantially homogeneous population of cultured human yolk sac stem cells displaying a phenotype of CD34⁻, MHC class I⁻ and MHC class II⁻ which are capable of giving rise to blood cells.

22. A cellular composition comprising a substantially homogeneous population of cultured human yolk sac stem cells displaying a phenotype of CD34⁻, MHC class I⁻ and MHC class II⁻ which are capable of forming tubular structures.

23. The composition of claim 21 or 22 wherein the yolk sac stem cells are isolated from a yolk sac prior to blood island formation.

24. The composition of claim 21 or 22 wherein the yolk sac stem cells are isolated from a human yolk sac at week 4 to week 8 of gestation.

25. A method of preparing a cellular composition of human yolk sac stem cells comprising:

(a) excising a yolk sac from a human embryo;

(b) detaching human yolk sac stem cells from yolk sac membrane; and (c) collecting a substantially homogeneous population of human yolk sac stem cells displaying a phenotype of $CD34^{31}$, MHC class $I^-$ and MHC class $II^-$ which are capable of giving rise to blood cells.

26. A method of preparing a cellular composition of human yolk sac stem cells comprising:

(a) excising a yolk sac from a human embryo;

(b) detaching human yolk sac stem cells from yolk sac membrane; and (c) collecting a substantially homogeneous population of human yolk sac stem cells displaying a phenotype of $CD34^-$, MHC class $I^-$ and MHC class $II^-$ which are capable of forming tubular structures.

27. A method of preparing a cellular composition of human yolk sac stem cells comprising:

(a) isolating a blastocyst or morula from a human;

(b) culturing the blastocyst or morula on a substratum containing a basement membrane preparation; and (c) collecting a substantially homogeneous population of human yolk sac stem cells displaying a phenotype of $CD34^-$, MHC class $I^-$ and MHC class $II^-$ which are capable of giving rise to blood cells.

28. A method of preparing a cellular composition of human yolk sac stem cells comprising:

(a) isolating a blastocyst or morula from a human;

(b) culturing the blastocyst or morula on a substratum containing a basement membrane preparation; and (c) collecting a substantially homogeneous population of human yolk sac stem cells displaying a phenotype of $CD34^-$, MHC class $I^-$ and MHC class $II^-$ which are capable of forming tubular structures.

29. A method of expanding a cellular composition of human yolk sac stem cells comprising culturing, in the presence of an agent which suppresses cellular differentiation, a substantially homogeneous population of human yolk sac stem cells displaying a phenotype of $CD34^-$, MHC class $I^-$ and MHC class $II^-$ which are capable of giving rise to blood cells.

30. A method of expanding a cellular composition of human yolk sac Stem cells comprising culturing, in the presence of an agent which suppresses cellular differentiation, a substantially homogeneous population of human yolk sac stem cells displaying a phenotype of $CD34^-$, MHC class $I^-$ and MHC class $II^-$ which are capable of forming tubular structures.

31. The method of claim 29 or 30 wherein the agent is leukemia inhibitory factor.

32. The method of claim 29 or 30 wherein the agent is stem-cell factor.

33. A method of producing blood cells in vitro, comprising culturing, in the presence of a growth factor, a substantially homogeneous population of human yolk sac stem cells displaying a phenotype of $CD34^-$, MHC class $I^-$ and MHC class $II^-$ which are capable of giving rise to blood cells.

34. The method of claim 33 wherein the growth factor is EPO, IL-2, IL-3, G-CSF, M-CSF, GM-CSF, or a combination thereof.

35. A method of producing endothelial cells in vitro, comprising culturing, in the presence of a growth factor, a substantially homogeneous population of human yolk sac stem cells displaying a phenotype of $CD34^-$, MHC class $I^-$ and MHC class $II^-$ which are capable of forming tubular structures.

36. The method of claim 35 wherein the growth factor is basic fibroblast growth factor.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

CTACCACGGA GACTTCTACA C                        21

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

GCACTCGGAG CAGAAGATGA T                        21

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

AGCTGTCGCT CTGTGGTTCT                          20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TGGGGAGAGT AAAGCCTATC                          20

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ATGGTGCACC TGACTGATGC TG                       22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GGTTTAGTGG TACTTGTGAG CC                       22

(2) INFORMATION FOR SEQ ID NO:7:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:7:

ACAGACTCAG AGAGAACCCA CCAT                              24

( 2 ) INFORMATION FOR SEQ ID NO:8:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:8:

GCTTAACGGT ATTTGGAGGT CAGC                              24

( 2 ) INFORMATION FOR SEQ ID NO:9:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:9:

CGTGGATGAA GTTGGTGGTG AG                                22

( 2 ) INFORMATION FOR SEQ ID NO:10:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:10:

ATTAGCCACA CCAGCCACCA CT                                22

( 2 ) INFORMATION FOR SEQ ID NO:11:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:11:

GGGCAAGGTG AATGTGGAAG AT                                22

( 2 ) INFORMATION FOR SEQ ID NO:12:

( i ) SEQUENCE CHARACTERISTICS:
    ( A ) LENGTH: 22 base pairs
    ( B ) TYPE: nucleic acid
    ( C ) STRANDEDNESS: single ( D ) TOPOLOGY: linear ( i i ) MOLECULE TYPE: DNA ( x i ) SEQUENCE DESCRIPTION: SEQ ID NO:12:

```
TGGTATCTGG AGGACAGGGC AC                                              2 2
```